United States Patent [19]

Tanaka et al.

[11] Patent Number: 5,587,516

[45] Date of Patent: Dec. 24, 1996

[54] ELECTROPHOTOGRAPHIC PHOTOCONDUCTOR COMPRISING PYRENYLAMINE DERIVATIVE, THE PYRENYLAMINE DERIVATIVE, INTERMEDIATE FOR PREPARATION THEREOF, AND METHOD FOR PREPARING THE PYRENYLAMINE DERIVATIVE AND THE INTERMEDIATE

[75] Inventors: Chiaki Tanaka, Shizuoka-ken; Masaomi Sasaki, Susono; Tamotsu Aruga, Mishima; Tomoyuki Shimada, Shizuoka-ken; Hiroshi Adachi, Numazu, all of Japan

[73] Assignee: Ricoh Company, Ltd., Tokyo, Japan

[21] Appl. No.: 463,739

[22] Filed: Jun. 5, 1995

Related U.S. Application Data

[62] Division of Ser. No. 427,124, Apr. 24, 1995, which is a division of Ser. No. 260,920, Jun. 15, 1994, Pat. No. 5,459,275, which is a continuation-in-part of Ser. No. 77,444, Jun. 17, 1993, abandoned, which is a continuation-in-part of Ser. No. 996,080, Dec. 23, 1992, Pat. No. 5,344,985.

[30] Foreign Application Priority Data

| Dec. 28, 1991 | [JP] | Japan | 3-360363 |
|---|---|---|---|
| Apr. 15, 1992 | [JP] | Japan | 4-121326 |
| Jun. 8, 1992 | [JP] | Japan | 4-173818 |
| Jun. 17, 1992 | [JP] | Japan | 4-183142 |
| Jul. 17, 1992 | [JP] | Japan | 4-213528 |
| Jul. 17, 1992 | [JP] | Japan | 4-213529 |
| Aug. 10, 1992 | [JP] | Japan | 4-234323 |
| Dec. 3, 1992 | [JP] | Japan | 4-350440 |
| Jun. 15, 1993 | [JP] | Japan | 5-168513 |

[51] Int. Cl.[6] ............................................. C07C 209/10
[52] U.S. Cl. .................. 564/405; 564/308; 564/408; 564/426; 548/131
[58] Field of Search ...................... 564/308, 405, 564/408, 426; 548/131

[56] References Cited

U.S. PATENT DOCUMENTS 5,488,164   1/1996   Shimada et al. ....................... 564/426

*Primary Examiner*—Brian M. Burn
*Attorney, Agent, or Firm*—Oblon, Spivak, McClelland, Maier & Neustadt, P.C.

[57] ABSTRACT

An electrophotographic photoconductor comprises an electroconductive substrate and a photoconductive layer formed thereon comprising as an effective component at least one pyrenylamine derivative of formula (I):

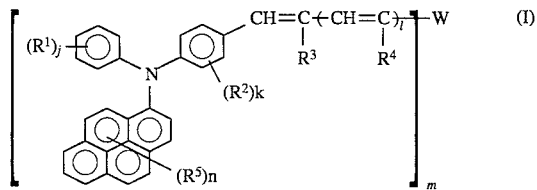

wherein $R^1$, $R^2$, $R^3$, $R^4$, $R^5$, W, j, k, l, m and n are specifically defined in the specification. Furthermore, a novel pyrenylamine derivative for use in the above electrophotographic photoconductor, an aldehyde compound, which is an intermediate for producing the pyrenylamine derivative, and methods of preparing the pyrenylamine derivative and the aldehyde compound are disclosed.

1 Claim, 7 Drawing Sheets

ELECTROPHOTOGRAPHIC PHOTOCONDUCTOR COMPRISING PYRENYLAMINE DERIVATIVE, THE PYRENYLAMINE DERIVATIVE, INTERMEDIATE FOR PREPARATION THEREOF, AND METHOD FOR PREPARING THE PYRENYLAMINE DERIVATIVE AND THE INTERMEDIATE

This is a Division of application Ser. No. 08/427,124 filed on Apr. 24, 1995, pending; which is a divisional of Ser. No. 08/260,920 filed on Jun. 15, 1994, allowed (U.S. Pat. No. 5,459,275); which is a Continuation-In-Part of Ser. No. 08/077,444 filed on Jun. 17, 1993, abandoned; which is a Continuation-In-Part of Ser. No. 07/996,080 filed on Dec. 23, 1992, U.S. Pat. No. 5,344,985.

BACKGROUND OF THE INVENTION

1. Field of the Invention

The present invention relates to an electrophotographic photoconductor, more particularly to an electrophotographic photoconductor comprising an electroconductive substrate and an electroconductive layer formed thereon comprising a pyrenylamine derivative, which is useful as an organic photoconductive material for use in the above-mentioned electrophotographic photoconductor and as a fluorescent whitening agent, an aldehyde compound serving as an intermediate for producing the pyrenylamine derivative, and methods for preparing the pyrenylamine derivative and the aldehyde compound.

2. Discussion of Background

Conventionally, inorganic materials such as selenium, cadmium sulfide and zinc oxide are used as photoconductive materials for electrophotographic photoconductors in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by toner particles comprising a coloring agent such as a dye or a pigment, and a binder agent such as a polymeric material, to a visible image.

Fundamental characteristics required for the photoconductor for use in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several short-comings from the viewpoint of practical use.

For instance, a selenium photoconductor, which is widely used at present, satisfies the above-mentioned requirements (1) to (3) completely, but it has the shortcomings that its manufacturing conditions are difficult, and accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be obtained by coating a dispersion of cadmium sulfide particles and zinc oxide particles respectively in a binder resin on a substrate. However, they are poor in mechanical properties, such as surface smoothness, hardness, tensile strength and wear resistance. Therefore, they cannot be used in the repeated operation.

In order to solve the problems of the inorganic materials, various electrophotographic photoconductors employing organic materials have been proposed recently and some are put to practical use. For example, there are known a photoconductor comprising poly-N-vinylcarbazole and 2,4,7-trinitrofluorene-9-one, as disclosed in U.S. Pat. No. 3,484,237; a photoconductor prepared by sensitizing poly-N-vinylcarbazole with a pigment of pyrylium salt, as disclosed in Japanese Patent Publication 48-25658; a photoconductor comprising as the main component an organic pigment, as disclosed in Japanese Laid-Open Patent Application 47-37543; a photoconductor comprising as the main component an eutectic crystal complex of a dye and a resin, as disclosed in Japanese Laid-Open Patent Application 47-10735; a photoconductor prepared by sensitizing a triphenylamine compound with a sensitizer pigment, as disclosed in U.S. Pat. No. 3,180,730; a photoconductor comprising an amine derivative as a charge transporting material, as disclosed in Japanese Laid-Open Patent Application 57-195254; a photoconductor comprising poly-N-vinylcarbazole and an amine derivative as charge transporting materials, as disclosed in Japanese Laid-Open Patent Application 58-1155; a photoconductor comprising a polyfunctional tertiary amine compound, in particular benzidine compound, as a photoconductive material, as disclosed in U.S. Pat. No. 3,265,496, Japanese Patent Publication 39-11546 and Japanese Laid-Open Patent Application 53-27033; a photoconductor comprising a stilbene derivative, as disclosed in Japanese Laid-Open Patent Applications 58-198425 and 58-189145; and a photoconductor comprising a triarylamine derivative, as disclosed in Japanese Laid-Open Patent Application 58-65440.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements in electrophotography.

SUMMARY OF THE INVENTION

It is therefore a first object of the present invention to provide an electrophotographic photoconductor comprising an electroconductive substrate and a photoconductive layer formed thereon comprising as an effective component at least one pyrenylamine derivative, free from the above-mentioned conventional shortcomings, which can completely satisfy all the requirements for the electrophotographic process, including high durability, and can be easily manufactured at a relatively low cost.

A second object of the present invention is to provide a novel pyrenylamine derivative for use in the above-mentioned electrophotographic photoconductor.

A third object of the present invention is to provide methods of preparing the above-mentioned novel pyrenylamine derivative.

A fourth object of the present invention is to provide a novel aldehyde compound serving as an intermediate for producing the above-mentioned novel pyrenylamine derivative.

A fifth object of the present invention is to provide a method of preparing the above-mentioned novel aldehyde compound.

The first object of the present invention can be achieved by an electrophotographic photoconductor comprising an electroconductive substrate and a photoconductive layer formed thereon comprising as an effective component at least one pyrenylamine derivative of formula (I):

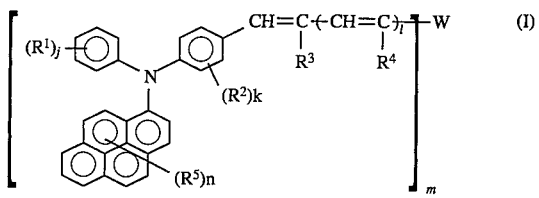

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or a phenyl group; $R^3$ and $R^4$ each represent hydrogen, cyano group, formyl group, an alkoxycarbonyl group, an alkyl group having 1 to 10 carbon atoms, an alkenyl group having 1 to 10 carbon atoms, or a phenyl group; $R^5$ represents hydrogen, an alkyl group having 1 to 10 carbon atoms, or an alkoxyl group having 1 to 10 carbon atoms; W represents hydrogen, an alkyl group having 1 to 10 carbon atoms, a phenylthio group, a bivalent chain unsaturated hydrocarbon group, a monovalent or bivalent carbocyclic aromatic group, or a monovalent or bivalent heterocyclic hydrocarbon group; and j is an integer of 1 to 5, k is an integer of 1 to 4, l is an integer of 0 to 2, m is an integer of 1 or 2, n is an integer of 1 to 3, provided that when j, k or n is 2 or more, $R^1$, $R^2$, or $R^5$ may be the same or different.

The second object of the present invention can be achieved by a pyrenylamine derivative of formula (Ia):

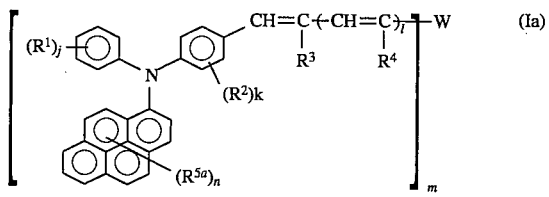

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or a phenyl group; and $R^3$ and $R^4$ each represent hydrogen, cyano group, formyl group, an alkoxycarbonyl group, an alkyl group having 1 to 10 carbon atoms, an alkenyl group having 1 to 10 carbon atoms, or a phenyl group; $R^{5a}$ represents hydrogen, or an alkyl group having 1 to 10 carbon atoms; W represents hydrogen, an alkyl group having 1 to 10 carbon atoms, a phenylthio group, a bivalent chain unsaturated hydrocarbon group, a monovalent or bivalent carbocyclic aromatic group, or a monovalent or bivalent heterocyclic hydrocarbon group; and j is an integer of 1 to 5, k is an integer of 1 to 4, l is an integer of 0 to 2, m is an integer of 1 or 2, n is an integer of 1 to 3, provided that when j, k or n is 2 or more, $R^1$, $R^2$, or $R^{5a}$ may be the same or different.

The third object of the present invention can be achieved by a method of preparing the pyrenylamine derivative of formula (Ia) comprising the step of allowing an aldehyde compound of formula (II) to react with a phosphorus compound of formula (III) in accordance with the following reaction scheme:

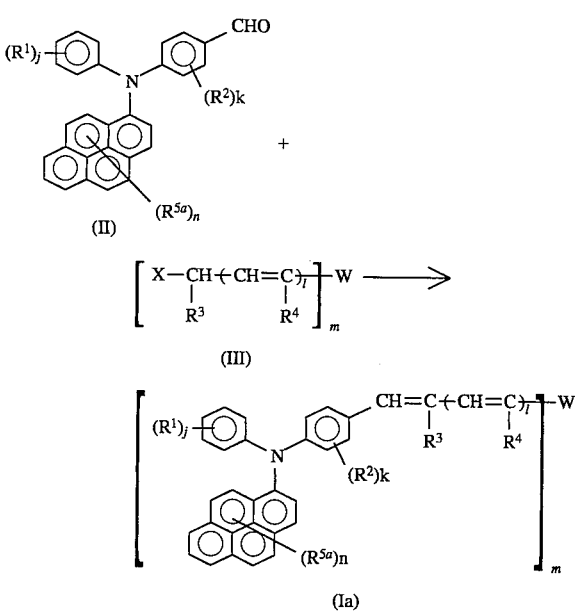

wherein $R^1$, $R^2$, $R^3$, $R^4$, $R^{5a}$, W, j, k, l, m and n are the same as defined in formula (Ia); X in formula (III) represents a phosphonium salt represented by $-P+(R^6)_3Y^-$, or a dialkylphosphite group represented by $-PO(OR^7)_2$, in which $R^6$ represents a phenyl group or an alkyl group having 1 to 10 carbon atoms, Y represents a halogen atom, and $R^7$ represents an alkyl group having 1 to 10 carbon atoms.

The third object of the present invention can also be achieved by a method of preparing the pyrenylamine derivative of formula (Ia) comprising the step of allowing a secondary amine compound of formula (IV) to react with a pyrene compound of formula (V) in accordance with the following reaction scheme:

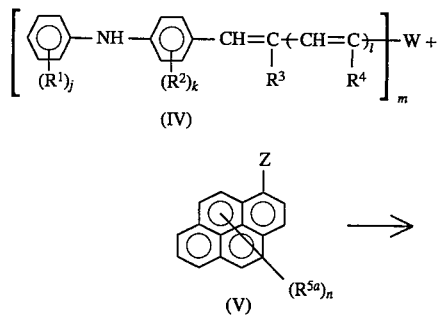

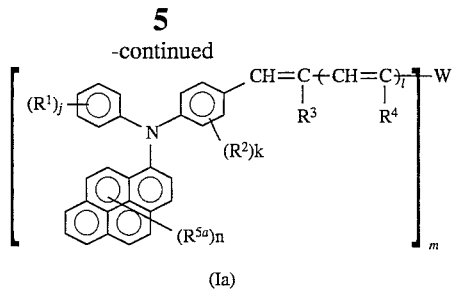

(Ia)

wherein $R^1$, $R^2$, $R^3$, $R^4$, $R^{5a}$, W, j, k, l, m and n are the same as defined in formula (Ia); and Z represents a halogen atom.

The fourth object of the present invention can be achieved by an aldehyde compound of formula (II):

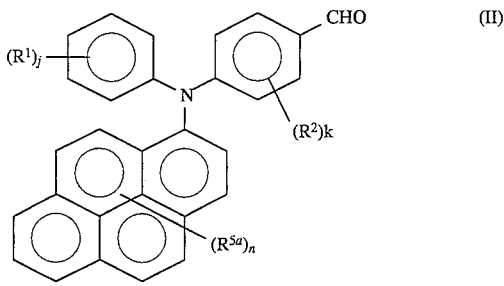

(II)

wherein $R^1$, $R^2$, $R^{5a}$, j, k and n are the same as defined in formula (Ia).

The fifth object of the present invention can be achieved by a method of preparing the aldehyde compound of formula (II) comprising the step of subjecting a diphenylaminopyrene compound of formula (VI) to formylation:

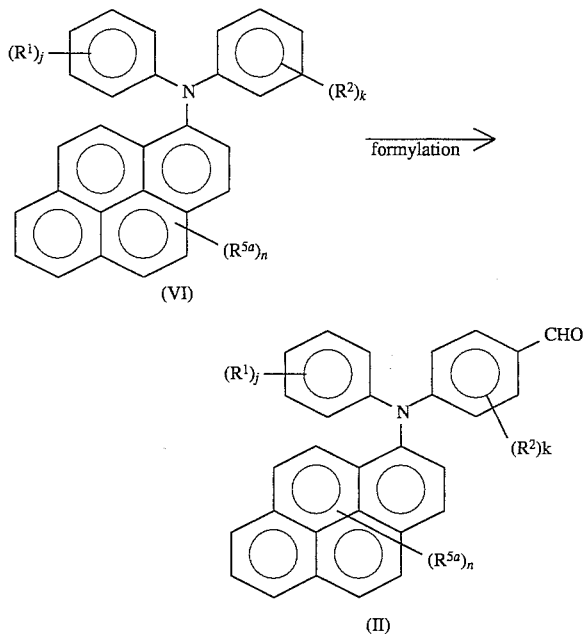

wherein $R^1$, $R^2$, $R^{5a}$, j, k and n are the same as defined in formula (Ia).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
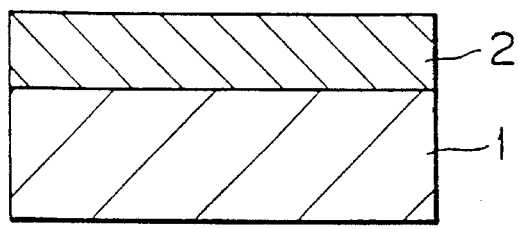
FIG. 1 is a schematic enlarged cross-sectional view of a first example of an electrophotographic photoconductor according to the present invention.

An electrophotographic photoconductor of the present invention comprises an electroconductive substrate and a photoconductive layer formed thereon comprising as an effective component at least one pyrenylamine derivative represented by the following formula (I):

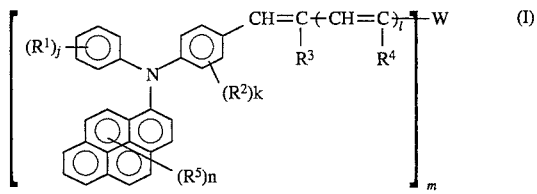

(I)

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or a phenyl group; $R^3$ and $R^4$ each represent hydrogen, cyano group, formyl group, an alkoxycarbonyl group, an alkyl group having 1 to 10 carbon atoms, an alkenyl group having 1 to 10 carbon atoms, or a phenyl group; $R^5$ represents hydrogen, an alkyl group having 1 to 10 carbon atoms, or an alkoxyl group having 1 to 10 carbon atoms; W represents hydrogen, an alkyl group having 1 to 10 carbon atoms, a phenylthio group, a bivalent chain unsaturated hydrocarbon group, a monovalent or bivalent carbocyclic aromatic group, or a monovalent or bivalent heterocyclic hydrocarbon group; and j is an integer of 1 to 5, k is an integer of 1 to 4, l is an integer of 0 to 2, m is an integer of 1 or 2, n is an integer of 1 to 3, provided that when j, k or n is 2 or more, $R^1$, $R^2$, or $R^5$ may be the same or different.

Examples of $R^1$, $R^2$, $R^3$, $R^4$, $R^5$, or W in formula (I) are as follows:

(1) A halogen atom such as fluorine, chlorine, bromine, or iodine.

(2) An alkyl group having 1 to 10 carbon atoms.

An example of the alkyl group having 1 to 10 carbon atoms is a straight chain or branched chain alkyl group having 1 to 12 carbon atoms, more preferably a straight chain or branched chain alkyl group having 1 to 9 carbon atoms, further preferably a straight chain or branched chain alkyl group having 1 to 4 carbon atoms.

This straight chain or branched chain alkyl group may have a substituent such as a fluorine atom, hydroxyl group, cyano group, an alkoxyl group having 1 to 4 carbon atoms, phenyl group, and a phenyl group having as a substituent a halogen atom, an alkyl group having 1 to 4 carbon atoms and an alkoxyl group having 1 to 4 carbon atoms.

Specific examples of the above alkyl group are methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(3) An alkoxyl group having 1 to 10 carbon atoms represented by —$OR^8$, in which $R^8$ represents the same alkyl group which may have a substituent as defined in (2).

Specific examples of the above alkoxyl group are methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group, and trifluoromethoxy group.

(4) An alkoxycarbonyl group represented by

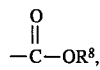

in which $R^8$ represents the same alkyl group which may have a substituent as defined in (2).

Specific examples of the above alkoxycarbonyl group are methoxycarbonyl group and ethoxycarbonyl group.

(5) Cyano group represented by —CN.

(6) Nitro group represented by —$NO_2$.

(7) Phenyl group represented by

in which $R^{11}$ represents hydrogen, or the same substituent as defined in (1) to (6) and (8) to (11) described later.

Specific examples of the above phenyl group are phenyl group, tolyl group, methoxyphenyl group, benzylphenyl group, chlorophenyl group, and 3,4-methylenedioxyphenyl group.

Examples of the substituent of $R^1$, $R^2$, $R^3$, $R^4$, $R^5$, or W in formula (I) are the above-mentioned groups in (1) to (7) and the following groups:

(8) An aryloxy group, in which an aryl group represents, for example, phenyl group or naphthyl group. The above aryloxy group may have a substituent such as an alkoxyl group having 1 to 4 carbon atoms, an alkyl group having 1 to 4 carbon atoms or a halogen atom.

Specific examples of the above aryloxy group are phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(9) An alkylthio group represented by —$SR^8$, or a phenylthio represented by

in which $R^8$ represents the same alkyl group as defined in (2).

Specific examples of the above alkylthio group are methylthio group, ethylthio group.

Specific examples of the above phenylthio group are phenylthio group and p-methylphenylthio group.

(10)

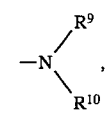

in which $R^9$ and $R^{10}$ and R independently represent hydrogen, the same alkyl group as defined in (2), or an aryl group. As the aryl group, phenyl group, biphenylyl group or naphthyl group can be employed, which may have a substituent such as an alkoxyl group having 1 to 4 carbon atoms, an alkyl group having 1 to 4 carbon atoms or a halogen atom. $R^9$ and $R^{10}$ may form a ring in combination, or in combination with carbon atoms on the aryl group.

Specific examples of the above

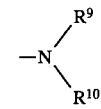

are an amino group, diethylamino group, N-methyl-N-phenylamino group, N,N-diphenylamino group, N,N-di(p-tolyl)amino group, dibenzylamino group, piperidino group, morpholino group and julolidyl group.

(11) An alkylenedioxy group such as methylenedioxy group, or an alkylenedithio group such as methylenedithio group.

When W in formula (I), (III) or (IV) is a bivalent unsaturated chain hydrocarbon group, specific examples of the bivalent unsaturated chain hydrocarbon group are vinylene group represented by —CH=CH—, and 1,3-butadienylene group represented by —CH=CH—CH=CH—.

When W in formula (I), (III) or (IV) is a monovalent or bivalent carbocyclic aromatic group, specific examples of the monovalent or bivalent carbocyclic aromatic group are non-condensed carbocyclic aromatic groups such as phenyl group, biphenyl group, and terphenyl group; and condensed polycyclic hydrocarbon groups such as pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group, and naphthacenyl.

When W in formula (I), (III) or (IV) is a monovalent or bivalent heterocyclic hydrocarbon group, specific examples of the monovalent or bivalent heterocyclic hydrocarbon group are pyridyl group, pyrimidyl group, pyrazinyl group, triazinyl group, furyl group, pyrrolyl group, thienyl group, quinolyl group, coumarinyl group, benzofuranyl group, benzimidazolyl group, benzoxazolyl group, dibenzo-furanyl group, benzothienyl group, dibenzothienyl group, indolyl group, carbazolyl group, pyrazolyl group, imidazolyl group, oxazolyl group, isooxazolyl group, thiazolyl group, indazolyl group, benzothiazolyl group, pyridazinyl group, cinnolinyl group, quinazolinyl group, quinoxalyl group, phthalazinyl group, phthalazinedionyl group, chromonyl group, naphtholactonyl group, quinolonyl group, o-sulfobenzoic acid imidyl group, maleic acid imidyl group, naphthalidinyl group, benzimidazolonyl group, benzoxazolonyl group, benzothiazolonyl group, benzothiazothionyl group, quinazolonyl group, quinoxalonyl group, phthalazonyl group, dioxopyrimidinyl group, pyridonyl group, isoquinolonyl group, isoquinolyl group, isothiazolyl group, benzisooxazolyl group, benzisothiazolyl group, indazolonyl group, acridinyl group, acridonyl group, quinazolinedionyl group, quinoxalinedionyl group, benzoxadinedionyl group, benzoxadinyl group, naphthalimidyl group, tetrahydrofuryl group, tetrahydrothienyl group, piperazino group, piperazinyl group and pyrrolidinyl group; and a bivalent cyclic aromatic group thereof. This monovalent or bivalent heterocyclic hydrocarbon group may have the same substituent as defined in (1) to (11).

Specific examples of the pyrenylamine derivative of formula (I) according to the present invention are shown in TABLE 1.

TABLE 1
| Comp. No. | (R¹)ⱼ | (R²)ₖ | R³ | R⁴ | (R⁵)ₙ | l | m | W |
|---|---|---|---|---|---|---|---|---|
| 1 | 4-CH₃ | H | H | — | H | 1 | 1 |  |
| 2 | 4-CH₃ | H |  | — | H | 0 | 1 |  |
| 3 | 4-CH₃ | H | H | H | H | 0 | 1 |  |
| 4 | 4-CH₃ | H | H | — | H | 1 | 1 |  |
| 5 | 4-CH₃ | H | H | — | H | 0 | 1 |  |
| 6 | 4-CH₃ | H | —CH₃ | — | H | 0 | 1 |  |

TABLE 1-continued

| | | | | | | | | Ar |
|---|---|---|---|---|---|---|---|---|
| 7 | 4-CH₃ | H | H | — | H | 0 | 1 | naphthyl |
| 8 | 4-CH₃ | H | H | — | H | 0 | 1 | pyrenyl |
| 9 | 4-CH₃ | H | H | — | H | 0 | 1 | 4-NH₂-C₆H₄ |
| 10 | 4-CH₃ | H | H | — | H | 0 | 1 | 4-N(CH₃)₂-C₆H₄ |
| 11 | 4-CH₃ | H | H | — | H | 0 | 1 | 4-C₂H₅-C₆H₄ |
| 12 | 4-CH₃ | H | H | — | H | 0 | 1 | 4-OC₂H₅-C₆H₄ |
| 13 | 2,4,6-tri CH₃ | 3,5-di CH₃ | 4-CH₃-C₆H₄ | C₆H₅ | 3,6,8-tri CH₃ | 1 | 1 | 4-NO₂-C₆H₄ |
| 14 | 3,5-di CH₃ | 2,6-di CH₃ | C₆H₅ | —CH₃ | 7-C(CH₃)₃ | 1 | 1 | 4-NO₂-C₆H₄ |

TABLE 1-continued
| | | | | | | | | |
|---|---|---|---|---|---|---|---|---|
| 15 | 4-CH$_3$ | H | H | — | H | 0 | 1 | 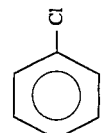 |
| 16 | 4-CH$_3$ | H | H | — | H | 0 | 1 | —CN |
| 17 | 4-CH$_3$ | H | H | — | H | 0 | 1 |  |
| 18 | 4-CH$_3$ | H | H | — | H | 0 | 1 |  |
| 19 | 4-CH$_3$ | H | H | — | H | 0 | 1 | —COOC$_2$H$_5$ |
| 20 | 4-CH$_3$ | H | H | — | H | 0 | 1 | 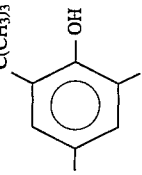 |
| 21 | 4-CH$_3$ | H | H | — | H | 0 | 1 | 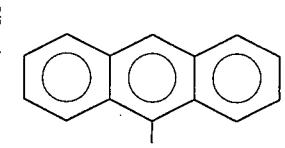 |
| 22 | 4-CH$_3$ | H | H | — | H | 0 | 1 | —C≡CH |
| 23 | 4-CH$_3$ | H | H | — | H | 0 | 1 | —CHO |

| | | | | | | |
|---|---|---|---|---|---|---|
| 24 | 4-CH₃ | H | H | — | H | 0 | 2 | 2,5-dimethoxyphenyl |
| 25 | 4-CH₃ | H | H | — | H | 0 | 2 | 9,10-anthracenediyl |
| 26 | 4-CH₃ | H | H | — | H | 0 | 2 | —CH=CH— |
| 27 | 4-CH₃ | H | H | — | H | 0 | 2 | 4,4'-biphenyldiyl |
| 28 | 4-CH₃ | H | H | — | H | 0 | 2 | 4,4'-stilbenediyl |
| 29 | 4-CH₃ | H | H | — | H | 0 | 2 | bis(4-methylbenzoyl)hydrazine-diyl |
| 30 | 4-CH₃ | H | H | — | H | 0 | 2 | 4-tolyl |
| 31 | H | H | H | — | H | 0 | 1 | phenyl |
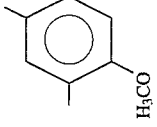

TABLE 1-continued
| | | | | | | | | |
|---|---|---|---|---|---|---|---|---|
| 32 | H | H | phenyl | — | H | 0 | | phenyl |
| 33 | H | H | H | H | H | 1 | 1 | phenyl |
| 34 | H | H | H | — | H | 0 | 1 | 4-methylphenyl (CH₃) |
| 35 | H | H | H | — | H | 0 | 1 | 4-methoxyphenyl (OCH₃) |
| 36 | H | H | —CH₃ | — | H | 0 | 1 | phenyl |
| 37 | H | H | H | — | H | 0 | 1 | naphthyl |
| 38 | H | H | H | — | H | 0 | 1 | pyrenyl |
| 39 | H | H | H | — | H | 0 | 1 | 4-aminophenyl (NH₂) |

TABLE 1-continued
| | | | | | | | |
|---|---|---|---|---|---|---|---|
| 40 | H | H | H | — | H | 0 | 1 | 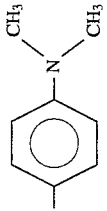 |
| 41 | 4-OCH₃ | H | H | — | H | 0 | 1 | 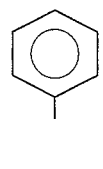 |
| 42 | 4-OCH₃ | H | phenyl | — | H | 0 | 1 |  |
| 43 | 4-OCH₃ | H | H | H | H | 1 | 1 | |
| 44 | 4-OCH₃ | H | H | — | H | 0 | 1 | 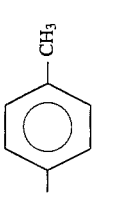 |
| 45 | 4-OCH₃ | H | H | — | H | 0 | 1 | 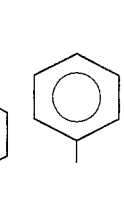 |
| 46 | 4-OCH₃ | H | —CH₃ | — | H | 0 | 1 | 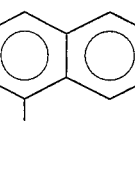 |
| 47 | 4-OCH₃ | H | H | — | H | 0 | 1 |  |

TABLE 1-continued

| # | | | | | | | | |
|---|---|---|---|---|---|---|---|---|
| 48 | 4-OCH₃ | H | H | — | H | 0 | 1 | pyren-1-ylmethyl |
| 49 | 4-OCH₃ | H | H | — | H | 0 | 1 | 4-NH₂-C₆H₄– |
| 50 | 4-OCH₃ | H | H | — | H | 0 | 1 | 4-N(CH₃)₂-C₆H₄– |
| 51 | 4-CH₃-C₆H₄– | H | H | — | H | 0 | 1 | C₆H₅-CH₂– |
| 52 | 4-CH₃-C₆H₄– | H | C₆H₅ | — | H | 0 | 1 | C₆H₅-CH₂– |
| 53 | 4-CH₃-C₆H₄– | H | H | H | H | 1 | 1 | C₆H₅-CH₂– |
| 54 | 4-CH₃-C₆H₄– | H | H | — | H | 0 | 1 | 4-CH₃-C₆H₄-CH₂– |
| 55 | 4-CH₃-C₆H₄– | H | H | — | H | 0 | 1 | 4-CH₃-C₆H₄-CH₂– |

TABLE 1-continued

| | | | | | | |
|---|---|---|---|---|---|---|
| 56 | 4-[phenyl] | H | —CH₃ | — | H | 0 | 1 | [phenyl] |
| 57 | 4-[phenyl] | H | H | — | H | 0 | 1 | [naphthyl] |
| 58 | 4-[tolyl] | H | H | — | H | 0 | 1 | [pyrenyl] |
| 59 | 4-[tolyl] | H | H | — | H | 0 | 1 | [phenyl-NH₂] |
| 60 | 4-[tolyl] | H | H | — | H | 0 | 1 | [phenyl-N(CH₃)₂] |
| 61 | 3-CH₃ | 3-CH₃ | [phenyl] | [phenyl] | 7-C(CH₃)₃ | 1 | 1 | [phenyl] |
| 62 | 4-[tolyl] | 2-CH₃ | —CH₃ | — | 3,6,8-tri CH₃ | 0 | 1 | [phenyl] |
| 63 | 3-CH₃ | 3-CH₃ | H | — | H | 0 | 1 | [phenyl] |

TABLE 1-continued

| # | | | | | | n | Ar |
|---|---|---|---|---|---|---|---|
| 64 | 3-CH$_3$ | 3-CH$_3$ | phenyl | — | H | — | phenyl |
| 65 | 4-CN | H | H | — | H | 0 | 3-methylphenyl |
| 66 | 4-CH$_3$ | H | H | — | 6-OCH$_3$ | 1 | biphenyl |
| 67 | 3-NO$_2$ | H | phenyl | — | H | 0 | phenyl |
| 68 | 4-CH$_3$ | H | phenyl | — | H | 1 | 4-methylphenyl |
| 69 | H | H | phenyl | — | H | 0 | 4-methylphenyl |
| 70 | 4-methylphenyl | H | phenyl | — | H | 1 | 4-methylphenyl |
| 71 | 4-CH$_3$ | H | H | — | H | 0 | 3,4-dimethylphenyl |
| 72 | H | H | H | — | H | 0 | 2,3-dimethylphenyl |

TABLE 1-continued

| | | | | | | | | |
|---|---|---|---|---|---|---|---|---|
| 73 | 4-OC₂H₅ | H | H | — | H | 0 | 1 | 3-methylphenoxyphenyl |
| 74 | 4-CH₃ | H | H | — | H | 0 | — | H |
| 75 | H | H | H | — | H | 0 | — | H |
| 76 | 4-CH₃ | H | H | — | H | 0 | 1 | 4-cyanophenyl |
| 77 | 4-CH₃ | H | H | — | H | 0 | 1 | 2-nitro-methylphenyl |
| 78 | 4-CH₃ | H | H | — | H | 0 | 1 | 3-nitrophenyl |
| 79 | 4-CH₃ | H | H | — | H | 0 | 1 | 4-nitrophenyl |
| 80 | 4-CH₃ | H | H | H | H | 1 | 1 | 2-nitro-methylphenyl |
| 81 | 4-CH₃ | H | H | H | H | 1 | 1 | 3-nitrophenyl |

TABLE 1-continued

| | | | | | | | |
|---|---|---|---|---|---|---|---|
| 82 | 4-CH₃ | H | H | — | H | 1 | 4-NO₂-phenyl |
| 83 | 4-OCH₃ | H | phenyl | — | H | 0 | 4-CH₃-phenyl |
| 84 | 4-OCH₃ | H | H | — | H | 0 | 2-phenyl |
| 85 | 4-phenyl | H | H | — | H | 0 | 2-phenyl |
| 86 | 4-phenyl | H | phenyl | — | H | 0 | 2-phenyl |
| 87 | 4-phenyl | H | phenyl | — | H | 0 | 2-phenyl |
| 88 | 4-phenyl | H | H | — | H | 0 | 4-CH₃-phenyl |
| 89 | 4-CH₃ | H | H | — | 7-C(CH₃)₃ | 0 | 2-phenyl |
| 90 | 4-CH₃ | H | —CH₃ | — | 7-C(CH₃)₃ | 0 | 2-phenyl |
| 91 | 4-CH₃ | H | phenyl | — | 7-C(CH₃)₃ | 0 | 2-phenyl |

TABLE 1-continued
| | | | | | | | |
|---|---|---|---|---|---|---|---|
| 92 | 4-CH$_3$ | H |  | — | 7-C(CH$_3$)$_3$ | 0 | 1 |  |
| 93 | 4-CH$_3$ | H | H | — | 7-C(CH$_3$)$_3$ | 0 | 2 |  |
| 94 | 4-CH$_3$ | H | H | —3 | 3,6,8-tri CH$_3$ | 0 | 1 |  |
| 95 | 4-CH$_3$ | H | —CH$_3$ | — | 3,6,8-tri CH$_3$ | 0 | 1 |  |
| 96 | 4-CH$_3$ | H |  | — | 3,6,8-tri CH$_3$ | 0 | 1 |  |
| 97 | 4-CH$_3$ | H |  | — | 3,6,8-tri CH$_3$ | 0 | 1 |  |
| 98 | 4-CH$_3$ | H | H | — | 3,6,8-tri CH$_3$ | 0 | 2 |  |
| 99 | 4-CH$_3$ | H | H | — | H | 0 | 2 |  |

The structure of the photoconductor of the present invention will now be explained making reference to FIGS. 1 to 5.

In the photoconductors according to the present invention, one or more of pyrenylamine derivatives of formula (I) are contained in the photoconductive layers 2, 2a, 2b, 2c and 2d. The pyrenylamine derivative can be employed in different ways, for example, as shown in FIGS. 1 to 5.

In the photoconductor shown in FIG. 1, a photoconductive layer 2 is formed on an electroconductive substrate 1, which photoconductive layer 2 comprises a pyrenylamine derivative, a sensitizing dye and a binder agent (binder resin). In this photoconductor, the pyrenylamine derivative works as a photoconductive material, through which charge carriers which are necessary for the light decay of the photoconductor are generated and transported. However, the pyrenylamine derivative itself scarcely absorbs light in the visible light range, so that it is necessary to add a sensitizing dye which absorbs light in the visible light range in order to form latent electrostatic images by use of visible light.

Figure 2:
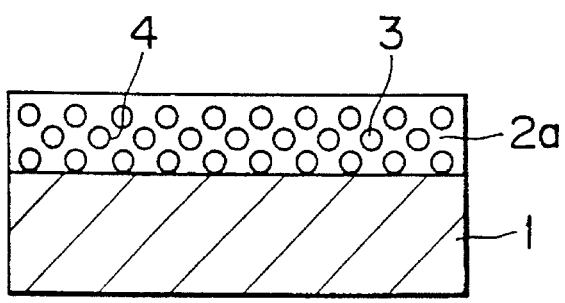
FIG. 2 is a schematic enlarged cross-sectional view of a second example of an electrophotographic photoconductor according to the present invention.

Referring to FIG. 2, there is shown a cross-sectional view of another embodiment of an electrophotographic photoconductor according to the present invention. In the figure, on the electroconductive substrate 1, there is formed a photoconductive layer 2a comprising a charge generating material 3 dispersed in a charge transporting medium 4 comprising a pyrenylamine derivative and a binder agent. In this embodiment, the pyrenylamine derivative and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is essential that the light-absorption wavelength regions of the charge generating material 3 and the pyrenylamine derivative do not overlap in the visible light range. This is because, in order to have the charge generating material 3 produce charge carriers efficiently, it is necessary to allow the light to reach the surface of the charge generating material 3. The pyrenylamine derivative of formula (I) scarcely absorb the light in the visible range. Therefore, especially when combined with the charge generating material 3 which absorbs the light in the visible region and generates charge carriers, the pyrenylamine derivative can work effectively as charge transporting materials.

Figure 3:
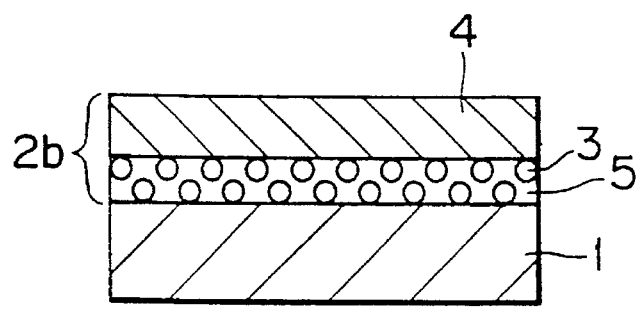
FIG. 3 is a schematic enlarged cross-sectional view of a third example of an electrophotographic photoconductor according to the present invention.

Referring to FIG. 3, there is shown a cross-sectional view of a further embodiment of an electrophotographic photoconductor according to the present invention. In the figure, there is formed on an electroconductive substrate 1, a two-layered photoconductive layer 2b comprising a charge generation layer 5 containing a charge generating material 3, and a charge transport layer 4 containing a pyrenylamine derivative.

In this photoconductor, the light which has passed through the charge transport layer 4 reaches the charge generation layer 5, where charge carriers are generated. The charge carriers which are necessary for the light decay for latent electrostatic image formation are generated by the charge generating material 3, and accepted and transported by the charge transport layer 4. In the charge transport layer 4, the pyrenylamine derivative mainly works for transportation of the charge carriers. The generation and transportation of the charge carriers are performed in the same mechanism as that in the photoconductor shown in FIG. 2.

Figure 4:
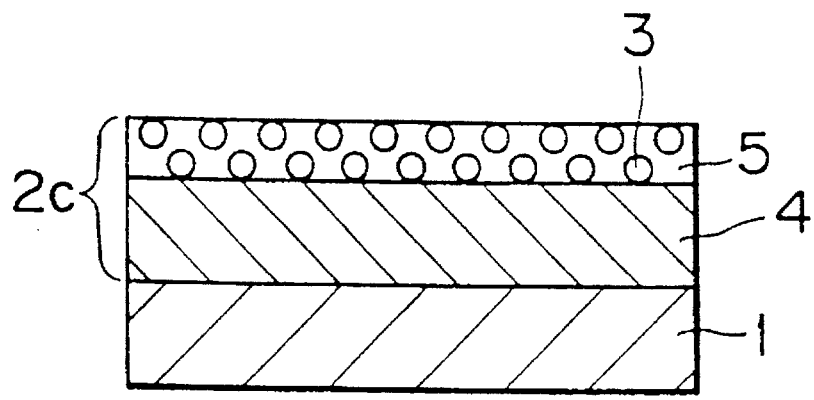
FIG. 4 is a schematic enlarged cross-sectional view of a fourth example of an electrophotographic photoconductor according to the present invention.

Referring to FIG. 4, there is shown still another embodiment of an electrophotographic photoconductor according to the present invention. In the figure, the overlaying order of a charge generation layer 5 and a charge transport layer 4 is reversed. The mechanism of the generation and transportation of charge carriers is the same as that of the photoconductor shown in FIG. 3.

Figure 5:
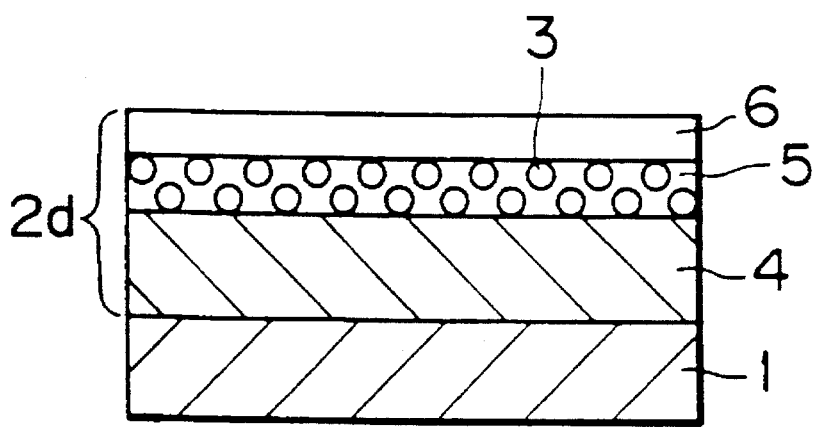
FIG. 5 is a schematic enlarged cross-sectional view of a fifth example of an electrophotographic photoconductor according to the present invention.

In the above photoconductor, a protective layer 6 may be formed on a charge generation layer 5 as shown in FIG. 5 for improving the mechanical strength thereof.

When the electrophotographic photoconductor according to the present invention shown in FIG. 1 is prepared, one or more of pyrenylamine derivatives of formula (I) are dispersed in a binder resin solution, and a sensitizing dye is then added to the mixture, so that a photoconductive layer coating liquid is prepared. The thus prepared photoconductive layer coating liquid is coated on the electroconductive substrate 1 and dried, so that the photoconductive layer 2 is formed on the electroconductive substrate 1.

It is preferable that the thickness of the photoconductive layer 2 be in the range of 3 to 50 μm, more preferably in the range of 5 to 20 μm. It is preferable that the amount of the pyrenylamine derivative contained in the photoconductive layer 2 be in the range of 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are as follows: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; a thiazine dye such as Methylene Blue; a cyanine dye such as cyanine; pyrylium dyes such as 2,6-diphenyl-4-(N,N-dimethylaminophenyl)thiapyrylium perchlorate and benzopyrylium salts (disclosed in Japanese Patent Publication 48-25658); and 2,4,7-trinitro-9-fluorenone, and 2,4-dinitro-9-fluorenone. These sensitizing dyes can be used alone or in combination.

The electrophotographic photoconductor shown in FIG. 2 can be obtained by dispersing finely-divided particles of the charge generating material 3 in the solution in which one or more of pyrenylamine derivatives and the binder agent are dissolved, coating the above prepared dispersion on the electroconductive substrate 1, and then drying the same to form the photoconductive layer 2a.

It is preferable that the thickness of the photoconductive layer 2a be in the range of 3 to 50 μm, more preferably in the range of 5 to 20 μm. It is preferable that the amount of the pyrenylamine derivative contained in the photoconductive layer 2a be in the range of 10 to 95 wt. %, more preferably in the range of 30 to 90 wt. %.

It is preferable that the amount of the charge generating material 3 contained in the photoconductive layer 2a be in the range of 0.1 to 50 wt. %, more preferably in the range of 1 to 20 wt. %.

Specific examples of the charge generating material 3 are as follows: inorganic pigments such as selenium, selenium—tellurium, cadmium sulfide, cadmium sulfide—selenium and α-silicone; and organic pigments, such as C.I. Pigment Blue 25 (C.I. 21180), C.I. Pigment Red 41 (C.I.

21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B (made by Bayer Co., Ltd.) and Indanthrene Scarlet R (made by Bayer Co., Ltd.). These charge generating materials may be used alone or in combination.

The electrophotographic photoconductor shown in FIG. 3 can be obtained as follows:

The charge generating material 3 is vacuum-deposited on the electroconductive substrate 1, or the dispersion in which finely-divided particles of the charge generating material 3 are dispersed in an appropriate solvent, together with the binder agent when necessary, is coated on the electroconductive substrate 1 and dried, so that the charge generation layer 5 is formed. When necessary, the charge generation layer 5 is subjected to surface treatment by buffing and adjustment of the thickness thereof. On the thus formed charge generation layer 5, a coating liquid in which one or more of pyrenylamine derivatives and the binder agent are dissolved is coated and dried, so that the charge transport layer 4 is formed. In the charge generation layer 5, the same charge generating material as employed in the previously mentioned photoconductive layer 2a can be used.

The thickness of the charge generation layer 5 is 5 μm or less, preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the pyrenylamine derivative contained in the charge transport layer 4 be in the range of 10 to 95 wt. %, more preferably in the range of 30 to 90 wt. %.

The electrophotographic photoconductor shown in FIG. 4 can be obtained as follows:

A coating liquid in which the pyrenylamine derivative and the binder agent are dissolved is coated on the electroconductive substrate 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The respective formulations of the charge generation layer and the charge transport layer are the same as previously described in FIG. 3.

The electrophotographic photoconductor shown in FIG. 5 can be obtained by forming the protective layer 6 on the charge generation layer 5 obtained in FIG. 4 by spray coating an appropriate resin solution. As a resin to be employed in the protective layer 6, any binder agents to be described later can be used.

Specific examples of materials for the electroconductive substrate 1 of the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl polymers such as polyvinylketone, polystyrene, poly-N-vinylcarbazole and polyacrylamide. All the resins having insulating properties and adhesive properties can be employed.

Some plasticizers may be added to the above-mentioned binder agent, when necessary. Examples of such plasticizers are halogenated paraffin, polybiphenyl chloride, dimethylnaphthalene and dibutyl phthalate.

Furthermore, in the electrophotographic photoconductors according to the present invention, an adhesive layer or a barrier layer can be interposed between the electroconductive substrate and the photoconductive layer when necessary. Examples of the material for use in the adhesive layer or the barrier layer are polyamide, nitrocellulose and aluminum oxide. It is preferable that the thickness of the adhesive layer or the barrier layer be 1 μm or less.

When copying is performed by use of the photoconductors according to the present invention, the surface of the photoconductor is charged uniformly in the dark to a predetermined polarity. The uniformly charged photoconductor is exposed to a light image, so that a latent electrostatic image is formed on the photoconductor. The thus formed latent electrostatic image is developed by a developer to a visible image, and when necessary, the developed image is transferred to a sheet of paper. The electrophotographic photoconductors according to the present invention have the advantages in that the photosensitivity is high and the flexibility is improved.

The novel pyrenylamine derivative of the present invention has the following formula (Ia):

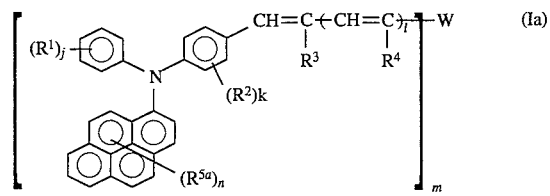

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or a phenyl group; $R^3$ and $R^4$ each represent hydrogen, cyano group, formyl group, an alkoxycarbonyl group, an alkyl group having 1 to 10 carbon atoms, an alkenyl group having 1 to 10 carbon atoms, or a phenyl group; $R^{5a}$ represents hydrogen, or an alkyl group having 1 to 10 carbon atoms; W represents hydrogen, an alkyl group having 1 to 10 carbon atoms, a phenylthio group, a bivalent chain unsaturated hydrocarbon group, a monovalent or bivalent carbocyclic aromatic group, or a monovalent or bivalent heterocyclic hydrocarbon group; and j is an integer of 1 to 5, k is an integer of 1 to 4, 1 is an integer of 0 to 2, m is an integer of 1 or 2, n is an integer of 1 to 3, provided that when j, k or n is 2 or more, $R^1$, $R^2$, or $R^{5a}$ may be the same or different.

When $R^3$ or $R^4$ represents an alkyl group in formula (Ia), specific examples of the alkyl group are methyl group, ethyl group, propyl group, and butyl group.

When $R^3$ or $R^4$ represents an alkenyl group in formula (Ia), specific examples of the alkenyl group are vinyl group, allyl group, isopropenyl group, butenyl group, pentenyl group, hexenyl group, heptenyl group, octenyl group, and nonenyl group.

The alkyl group, alkenyl group or the phenyl group represented by $R^3$ or $R^4$ in formula (Ia) may have a substituent.

Examples of the substituent of the alkyl group and alkenyl group are alkoxyl group having 1 to 4 carbon atoms, and a halogen atom.

Examples of the substituent of the phenyl group represented by $R^3$ or $R^4$ in formula (Ia) are an alkyl group having 1 to 4 carbon atoms, an alkoxyl group having 1 to 4 carbon atoms, an alkylenedioxy group such as methylenedioxy group or ethylenedioxy group, and a halogen atom.

The pyrenylamine derivative of formula (Ia) can be prepared by allowing an aldehyde compound of formula (II) to react with a phosphorus compound of formula (III) in accordance with the following reaction scheme:

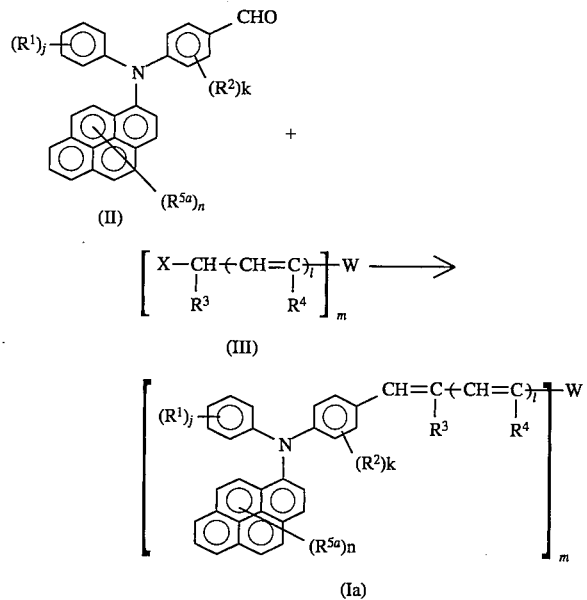

wherein $R^1$, $R^2$, $R^3$, $R^4$, $R^{5a}$, W, j, k, l, m and n are the same as defined in formula (Ia); and X in formula (III) represents a phosphonium salt represented by $-P^+(R^6)_3Y^-$, or a dialkylphosphite group represented by $-PO(OR^7)_2$, in which $R^6$ represents a phenyl group or an alkyl group having 1 to 10 carbon atoms, Y represents a halogen atom, and $R^7$ represents an alkyl group having 1 to 10 carbon atoms.

The pyrenylamine derivative of formula (Ia) can also be prepared by allowing a secondary amine compound of formula (IV) to react with a pyrene compound of formula (V) in accordance with the following reaction scheme:

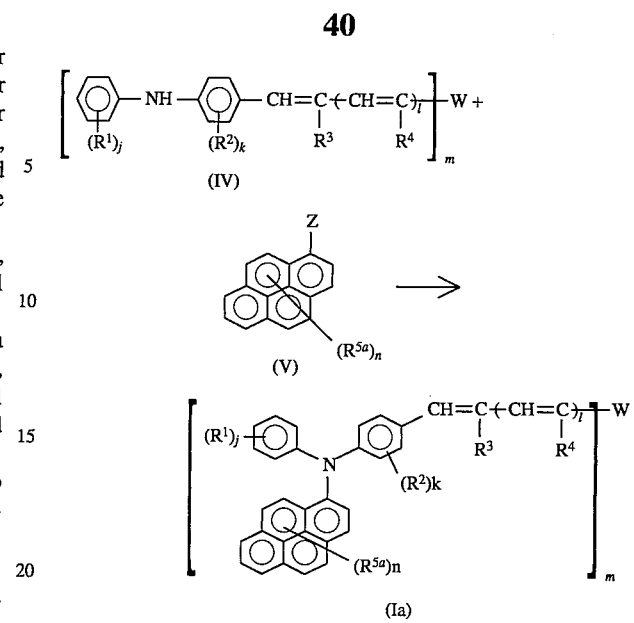

wherein $R^1$, $R^2$, $R^3$, $R^4$, $R^{5a}$, W, j, k, l, m and n are the same as defined in formula (Ia); and Z represents a halogen atom.

In the first mentioned method for producing the pyrenylamine derivative of formula (Ia), the aldehyde compound of formula (II) is allowed to react with a phosphorus compound of formula (III) in the presence of a basic catalyst at room temperature to about 100° C.

Examples of the basic catalyst for use in the above method are sodium hydroxide, potassium hydroxide, sodium amide, and sodium hydride; and alcoholates such as sodium methylate, and potassium-t-butoxide.

Examples of the reaction solvent for use in the above mentioned method are methanol, ethanol, isopropanol, butanol, 2-methoxyethanol, 1,2-dimethoxyethane, bis(2-methoxyethyl)ether, dioxane, tetrahydrofuran, benzene, toluene, xylene, dimethylsulfoxide, N,N-dimethylformamide, N-methylpyrrolidone, and 1,3-dimethyl-2-imidazolidinone. Of these solvents, polar solvents such as N,N-dimethylformamide and dimethylsulfoxide are preferably employed.

The reaction temperature can be selected from a relatively wide range, depending upon (1) the stabilization of the reaction solvent used in the reaction to the basic catalyst, (2) the condensation reactivities of the compounds of formulas (Ia), (II), (III) and (IV), and (3) the reactivity of the basic catalyst as a condensation agent in the reaction solvent.

For example, when a polar solvent is employed as the reaction solvent, the reaction temperature can be set in the range of from room temperature to 100° C. in practice, preferably in the range of from room temperature to 80° C. However, in the case where the reaction time is shortened, or a condensation agent with low activity is employed in the reaction, the reaction temperature may be increased.

In the second method for producing the pyrenylamine derivative of formula (Ia) of the present invention, the secondary amine compound of formula (IV) and the pyrene compound of formula (V) are allowed to react with the addition thereto of copper powder, copper oxide, or copper halogenide and an alkaline material in a sufficient amount to neutralize hydrogen halogenide which is produced in the course of the condensation reaction thereof, in the presence or absence of a reaction solvent in an atmosphere of nitrogen at about 150° to 250° C.

Examples of the alkaline material for use in the above method are sodium hydroxide, potassium hydroxide, sodium carbonate, and potassium carbonate.

Examples of the reaction solvent used in the above reaction are nitrobenzene, dichlorobenzene, quinoline, N,N-dimethylformamide, dimethylsulfoxide, N-methylpyrrolidone, and 1,3-dimethyl-2-imidazolidinone.

The novel pyrenylamine derivatives of formula (Ia) of the present invention are remarkably effective as photoconductive materials for use in an electrophotographic photoconductor, and can be optically or chemically sensitized with a sensitizer such as a dye or a Lewis acid. In addition, the above pyrenylamine derivatives effectively function as charge transporting materials in a function-separating type electrophotographic photoconductor in which an organic or inorganic pigment serves as a charge generating material.

The aldehyde compound of the present invention can be used as an intermediate for producing the pyrenylamine derivative of the present invention of formula (II):

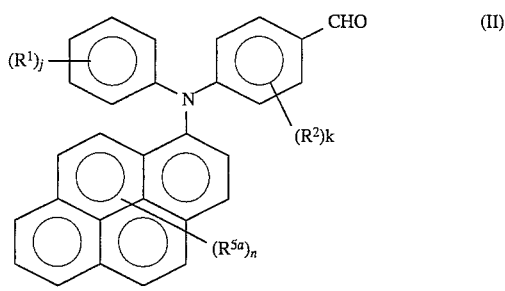

(II)

wherein $R^1$, $R^2$, $R^{5a}$, j, k and n are the same as defined in formula (Ia).

When $R^1$, $R^2$ or $R^{5a}$ represents an alkyl group in (II), specific examples of the alkyl group are methyl group, ethyl group, propyl group, and butyl group.

When $R^1$ or $R^2$ represents an alkoxyl group in formula (II), specific examples of the alkoxyl group are methoxy group, ethoxy group, and propoxy group.

The alkyl group or alkoxyl group represented by $R^1$, $R^2$ or $R^{5a}$ in the formula (II) may have a substituent.

Examples of the substituent of the alkyl group represented by $R^1$, $R^2$ or $R^{5a}$ in the formula (II) are phenyl group, a halogen atom, an alkoxyl group having 1 to 4 carbon atoms, and an aryloxy group.

An example of the substituent of the alkoxyl group is a straight chain or branched chain alkyl group having 1 to 12 carbon atoms, more preferably a straight chain or branched chain alkyl group having 1 to 9 carbon atoms, further preferably a straight chain or branched chain alkyl group having 1 to 4 carbon atoms. This straight chain or branched chain alkyl group may have a substituent such as a fluorine atom, hydroxyl group, cyano group, an alkoxyl group having 1 to 4 carbon atoms, phenyl group, and a phenyl group having as a substituent a halogen atom, an alkyl group having 1 to 4 carbon atoms and an alkoxyl group having 1 to 4 carbon atoms.

Specific examples of the above straight chain or branched chain alkyl group are methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group, and 4-phenylbenzyl group.

The phenyl group which is a substituent of the alkyl group represented by $R^1$ or $R^2$ in formula (II) may have a substituent.

Examples of the substituent of the phenyl group represented by $R^1$ or $R^2$ in the formula (II) are an alkyl group such as methyl group, ethyl group, ethoxy group, or propoxy group; an alkoxyl group such as methoxy group, ethoxy group, or propoxy group; and a halogen atom such as bromine, chlorine, or fluorine.

The novel aldehyde compound of formula (II) of the present invention can be produced by subjecting a diphenylaminopyrene compound of formula (VI) to formylation in accordance with the following reaction scheme:

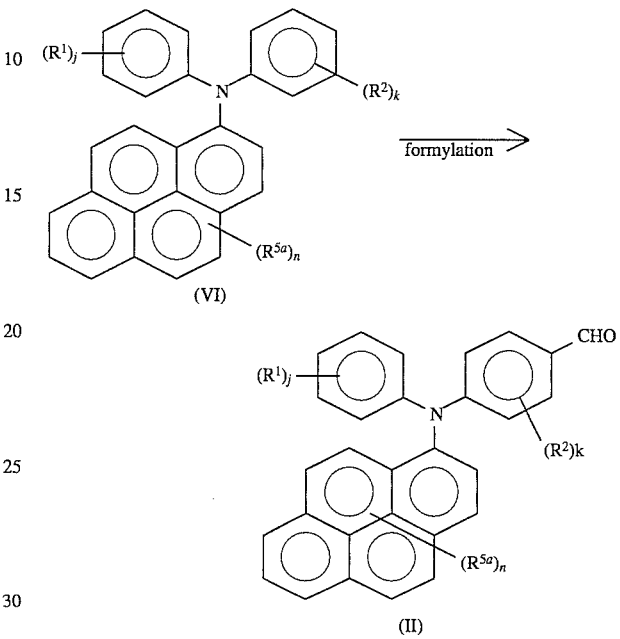

wherein $R^1$, $R^2$, $R^{5a}$, j, k, and n are the same as defined in formula (Ia).

More specifically, the above aldehyde compound of formula (II) can be produced by allowing the diphenylaminopyrene compound of formula (VI) to react with a vilsmeier reagent to obtain an immonium salt intermediate, and then hydrolyzing the immonium salt intermediate.

The Vilsmeier reagent used in the above reaction can be prepared by use of a conventional method of allowing an amide such as N,N-dimethylformamide or N-methylformanilide to react with an acid halide such as phosphoryl chloride, phosphoryl bromide, oxalyl chloride, phosgene, thionyl chloride, triphenylphosphine-bromine, or hexachlorotriphosphazatriene in an amount equimolar with the amide.

The amount of the Vilsmeier reagent may be a stoichiometric amount with the respect to the diphenylaminopyrene compound of formula (VI), but it is preferable that the Vilsmeier reagent be used in an amount more than the equimolar amount with respect to the diphenylaminopyrene compound of formula (VI).

The aldehyde compound of formula (II) can be prepared by either of the following two methods according to the present invention:

(i) A method of allowing a Vilsmeier reagent which has already been prepared to react with diphenylaminopyrene compound of formula (VI) in solvent, thereby preparing the aldehyde compound; and (ii) A method of adding dropwise the previously mentioned acid halide to a solution containing the diphenylaminopyrene compound of formula (VI) and the previously mentioned amide to prepare the Vilsmeier reagent and simultaneously allow the diphenylaminopyrene compound to react with the Vilsmeier reagent, thereby preparing the aldehyde compound.

Examples of the reaction solvent employed in the above-mentioned method are an inert aromatic hydrogen-carbonate such as benzene; chloroform; dichloroethane; and o-dichlorobenzene. In addition, the previously mentioned amides themselves can also be employed as the reaction solvents.

It is preferable that the reaction temperature be in the range of 0° to 150° C., more preferably in the range of 20° to 80° C.

The immonium salt obtained by allowing the diphenylaminopyrene compound of formula (VI) to react with the Vilsmeier reagent is hydrolyzed by water or an aqueous alkaline solution, so that the aldehyde compound of formula (II) of the present invention can be derived therefrom.

Examples of the aqueous alkaline solution are an aqueous solution of sodium hydroxide, an aqueous solution of potassium hydroxide, an aqueous solution of sodium acetate, and an aqueous solution of potassium acetate.

The diphenylaminopyrene compound of formula (VI) can easily be prepared by use of the method described in Japanese Patent Application 2-321723.

Other features of this invention will become apparent in the course of the following description of exemplary embodiments, which are given for illustration of the invention and are not intended to be limiting thereof.

EXAMPLE 1-1

[Synthesis of N-(4-formylphenyl)-N-(4-methylphenyl)-1-aminopyrene]

5.15 g (33.6 mmol) of phosphorus oxychloride was added dropwise to 29.24 g (400 mmol) of N,N-dimethylformamide at 0° to 3° C. over a period of 17 minutes under an ice-cooled condition, whereby a Vilsmeier reagent was produced.

To the Vilsmeier reagent thus obtained, 10.74 g (28.0 mmol) of N-phenyl-N-(4-methylphenyl)-1-aminopyrene was added. The mixture was warmed to room temperature with stirring over a period of 30 minutes and further stirred at 70° to 75° C. for five hours.

The mixture was then cooled to room temperature and poured into 300 ml of iced water. This mixture was made basic with the addition of an aqueous solution of sodium hydroxide (20 wt. %) and stirred for one hour, whereby a yellow precipitate was obtained.

The yellow precipitate thus obtained was extracted with toluene. The extracting toluene layer was washed with water, and dried over anhydrous magnesium sulfate. Toluene was distilled away from the extracting toluene solution under reduced pressure, whereby an oily orange material was obtained.

The oily material thus obtained was subjected to silica gel column chromatography using toluene as an eluting solvent to obtain a product. The product was recrystallized from a mixed solvent of ethanol and ethyl acetate, so that 9.47 g of N-(4-formylphenyl)-N-(4-methylphenyl)-1-aminopyrene was obtained as yellow needle crystals in a yield of 82.2%. The melting point of the above compound was 172.5° to 174.5° C.

The results of the elemental analysis of the above compound were as follows:

|        | % C   | % H  | % N  |
|--------|-------|------|------|
| Found  | 87.66 | 5.06 | 3.40 |
| Calcd. | 87.56 | 5.14 | 3.40 |

The above calculation was based on the formula for N-(4-formylphenyl)-N-(4-methylphenyl)-1-aminopyrene of $C_{30}H_{21}NO$.

Figure 6:
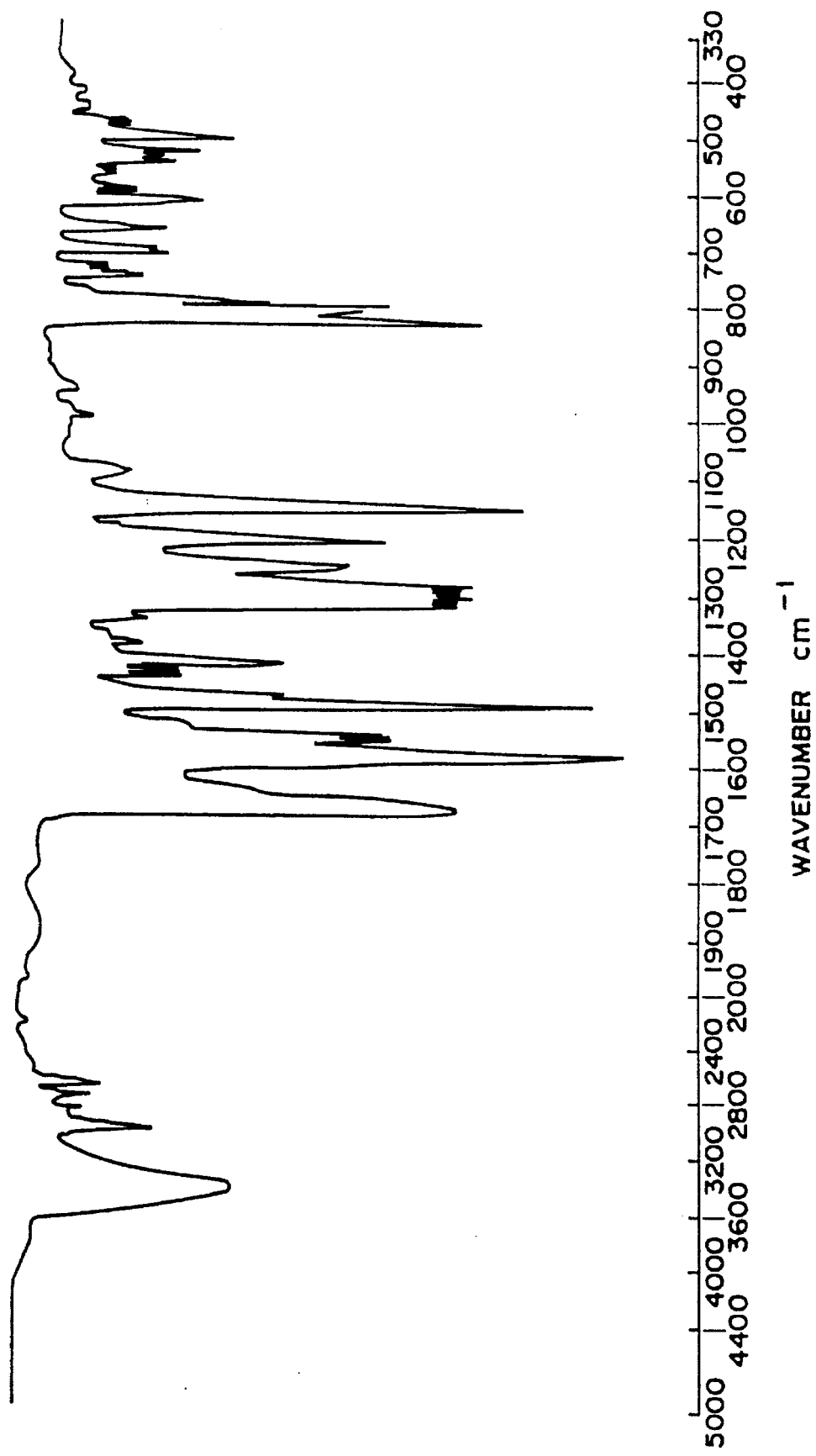
FIG. 6 is an IR absorption spectrum of an aldehyde compound obtained in Example 1-1 by use of a KBr tablet.

FIG. 6 shows an IR absorption spectrum of the above aldehyde compound taken by use of a KBr tablet.

The IR absorption spectrum indicates the appearance of the characteristic absorption peaks of vC-H (aldehyde) at 2820 cm$^{-1}$ and 2740 cm$^{-1}$, and the characteristic absorption peak of vC=O (aldehyde) at 1680 cm$^{-1}$.

EXAMPLE 1-2

The procedure for preparation of N-(4-formylphenyl)-N-(4-methylphenyl)-1-aminopyrene in Example 1-1 was repeated except that the N,N-dimethylformamide employed in Example 1-1 was replaced by N-methylformanilide, so that an aldehyde compound of the present invention was obtained as shown in TABLE 2.

Figure 7:
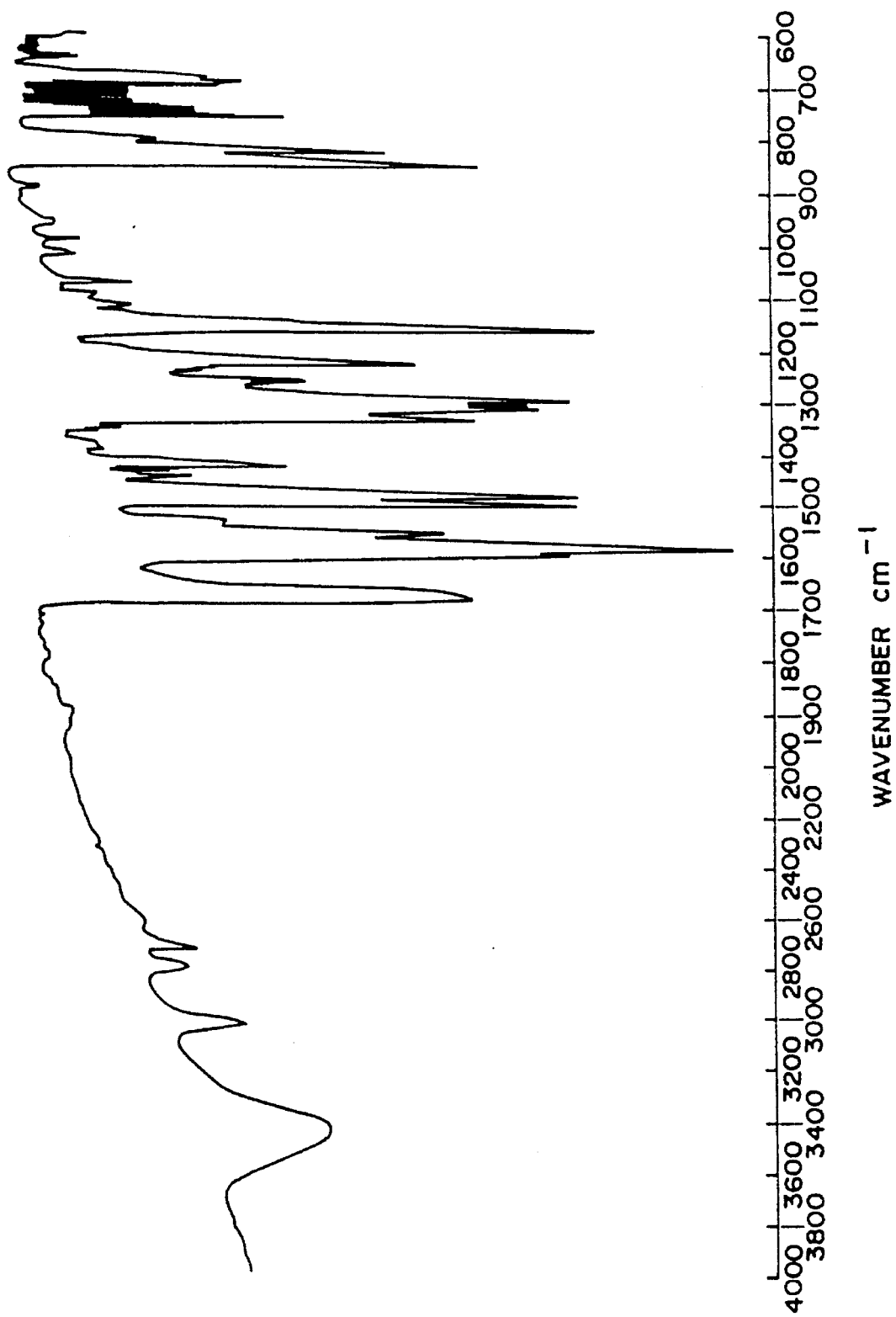
FIG. 7 is an IR absorption spectrum of an aldehyde compound obtained in Example 1-2 by use of a KBr tablet.

FIG. 7 shows an IR absorption spectrum of the above obtained aldehyde compound taken by use of a KBr tablet.

EXAMPLE 1-3

The procedure for preparation of N-(4-formylphenyl)-N-(4-methylphenyl)-1-aminopyrene in Example 1-1 was repeated except that the N,N-dimethylformamide, and the mixed solvent of ethanol and ethyl acetate employed in Example 1-1 were respectively replaced by N-methylformanilide and a mixed solvent of toluene and ethanol, so that an aldehyde compound of the present invention was obtained as shown in TABLE 2.

Figure 8:
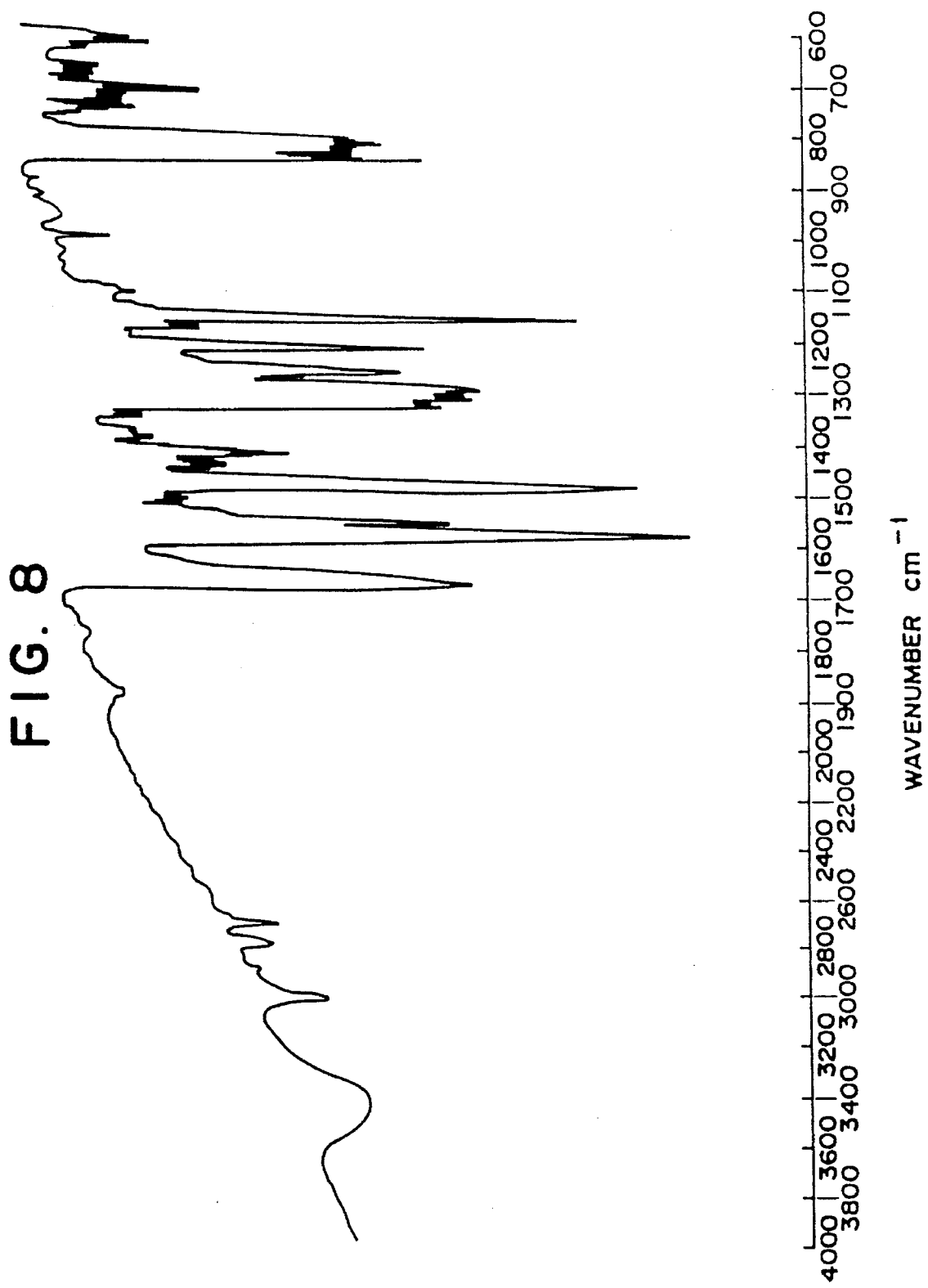
FIG. 8 is an IR absorption spectrum of an aldehyde compound obtained in Example 1-3 by use of a KBr tablet.

FIG. 8 shows an IR absorption spectrum of the above aldehyde compound taken by use of a KBr tablet.

TABLE 2

| Example No. | Aldehyde Compound | Melting Point (°C.) (Solvent for Recrystallization) | Elemental Analysis Found (Calcd.) | | |
|---|---|---|---|---|---|
| | | | % C | % H | % N |
| 1-2 | 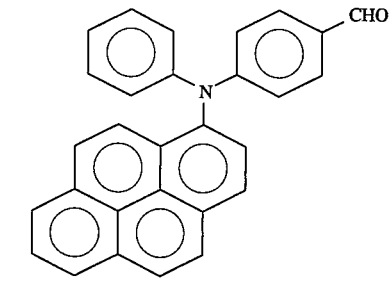 | 149.0–152.0 (Ethyl acetate-ethanol) | 87.86 (87.63) | 5.05 (4.82) | 3.61 (3.52) |

TABLE 2-continued

| Example No. | Aldehyde Compound | Melting Point (°C.) (Solvent for Recrystallization) | Elemental Analysis Found (Calcd.) | | |
|---|---|---|---|---|---|
| | | | % C | % H | % N |
| 1-3 | H₃C—⟨phenyl⟩—⟨phenyl⟩—N(1-pyrenyl)—⟨phenyl⟩—CHO | 185.5–187.5 (Toluene-ethanol) | 88.66 (88.68) | 5.35 (88.68) | 2.75 (2.87) |

EXAMPLE 2-1

[Synthesis of N-(4-methylphenyl)-N-(4-styrylphenyl)-1-aminopyrene (Compound No. 1 in TABLE 1)]

2.47 g (6.0 mmol) of the N-(4-formylphenyl)-N-(4-methylphenyl)-1-aminopyrene synthesized in Example 1-1 and 1.64 g (7.2 mmol) of diethyl benzylphosphonate were added to 30 ml of N,N-dimethylformamide. To the mixture thus obtained, 1.39 g (7.2 mmol) of a 25% methanol solution of sodium methylate was added dropwise over a period of 10 minutes. The above mixture was stirred at room temperature for three hours, poured into 200 ml of iced water, neutralized by the addition of acetic acid, and further stirred for 30 minutes.

A precipitate was formed in the mixture. The precipitate was separated by filtration, washed successively with water and methanol, and dried, so that 2.78 g of a crude material was obtained in a yield of 95.2%.

The thus obtained material was subjected to silica gel column chromatography using a mixed solvent of toluene and n-hexane with a volume ratio of 1:3 as an eluting solution. The product was recrystallized from a mixed solvent of ethanol and ethyl acetate, so that 1.87 g of N-(4-methylphenyl)-N-(4-styrylphenyl)-1-aminopyrene (Compound No. 1) was obtained as yellow needle crystals in a yield of 64.0%. The melting point of the above compound was 142.8° C. (TG-DTA endothermic peak temperature).

The results of the elemental analysis of the above compound were as follows:

| | % C | % H | % N |
|---|---|---|---|
| Found | 91.62 | 5.56 | 2.82 |
| Calcd. | 91.51 | 5.61 | 2.88 |

The above calculation was based on the formula for N-(4-methylphenyl)-N-(4-styrylphenyl)-1-aminopyrene of $C_{37}H_{27}N$.

Figure 9:
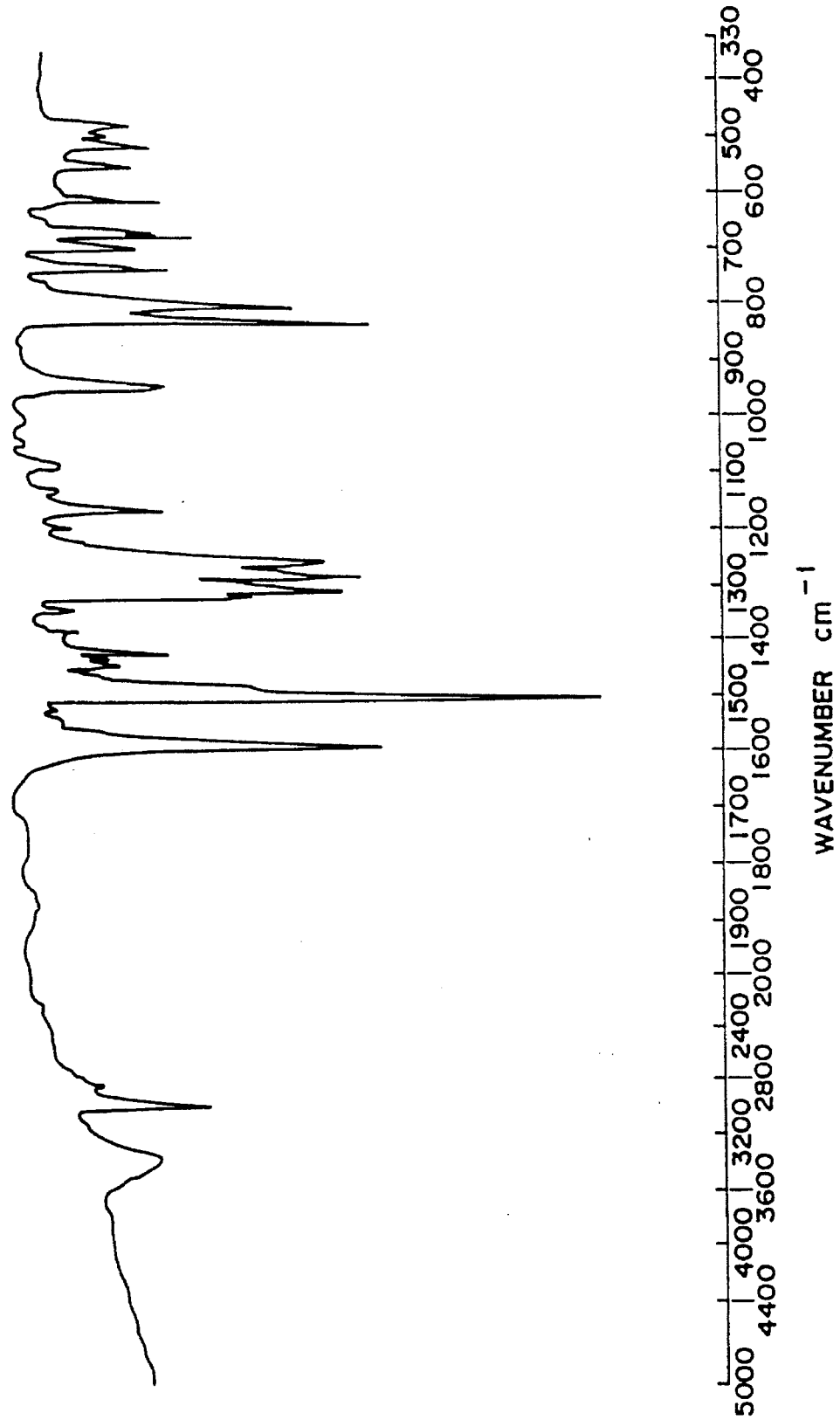
FIG. 9 is an IR absorption spectrum of N-(4-methylphenyl)-N-(4-styrylphenyl)-1-aminopyrene obtained in Example 2-1 by use of a KBr tablet.

FIG. 9 shows an IR absorption spectrum of the N-(4-methylphenyl)-N-(4-styrylphenyl)-1-aminopyrene taken by use of a KBr tablet.

The IR absorption spectrum of the above obtained compound indicates the appearance of the characteristic absorption peak based on the C-H out-of-plane the deformation vibration of the trans-olefin in the compound at 965 cm⁻¹.

EXAMPLE 2-2

[Synthesis of 1,4-bis-[N-(1-pyrenyl)-N-(4-methylphenyl)-4-aminostyryl]benzene (Compound No. 30 in TABLE 1)]

3.30 g (8.0 mmol) of the N-(4-formylphenyl)-N-(4-methylphenyl)-1-aminopyrene synthesized in Example 1-1 and 1.51 g (4.0 mmol) of tetraethyl p-xylylenedi-phosphonate were added to 30 ml of N,N-dimethylformamide. To the mixture thus obtained, 1.86 g (9.6 mmol) of a 25% methanol solution of sodium methylate was added dropwise over a period of 25 minutes at room temperature, followed by stirring the mixture at room temperature for ten hours. The above mixture was then poured into 100 ml of methanol, and stirred for 1.5 hours.

A precipitate was formed in the mixture. The precipitate was separated from the mixture by filtration, washed with water twice and with methanol once, and then separated by filtration, so that 2.81 g of a crude material was obtained in a yield of 78.7%.

The thus obtained material was subjected to silica gel column chromatography using toluene as an eluting solution. The product was recrystallized successively from N,N-dimethylformamide and a mixed solvent of toluene and dioxane, so that 1,4-bis-[N-(1-pyrenyl)-N-(4-methylphenyl)-4-aminostyryl]benzene (Compound No. 30) was obtained as yellow needle crystals. The melting point of the above compound was 280° C. or more.

The results of the elemental analysis of the above compound were as follows:

| | % C | % H | % N |
|---|---|---|---|
| Found | 91.52 | 5.31 | 3.12 |
| Calcd. | 91.45 | 5.42 | 3.14 |

The above calculation was based on the formula for 1,4-bis-[N-(1-pyrenyl)-N-(4-methylphenyl)-4-aminostyryl]benzene of $C_{68}H_{48}N_2$.

Figure 10:
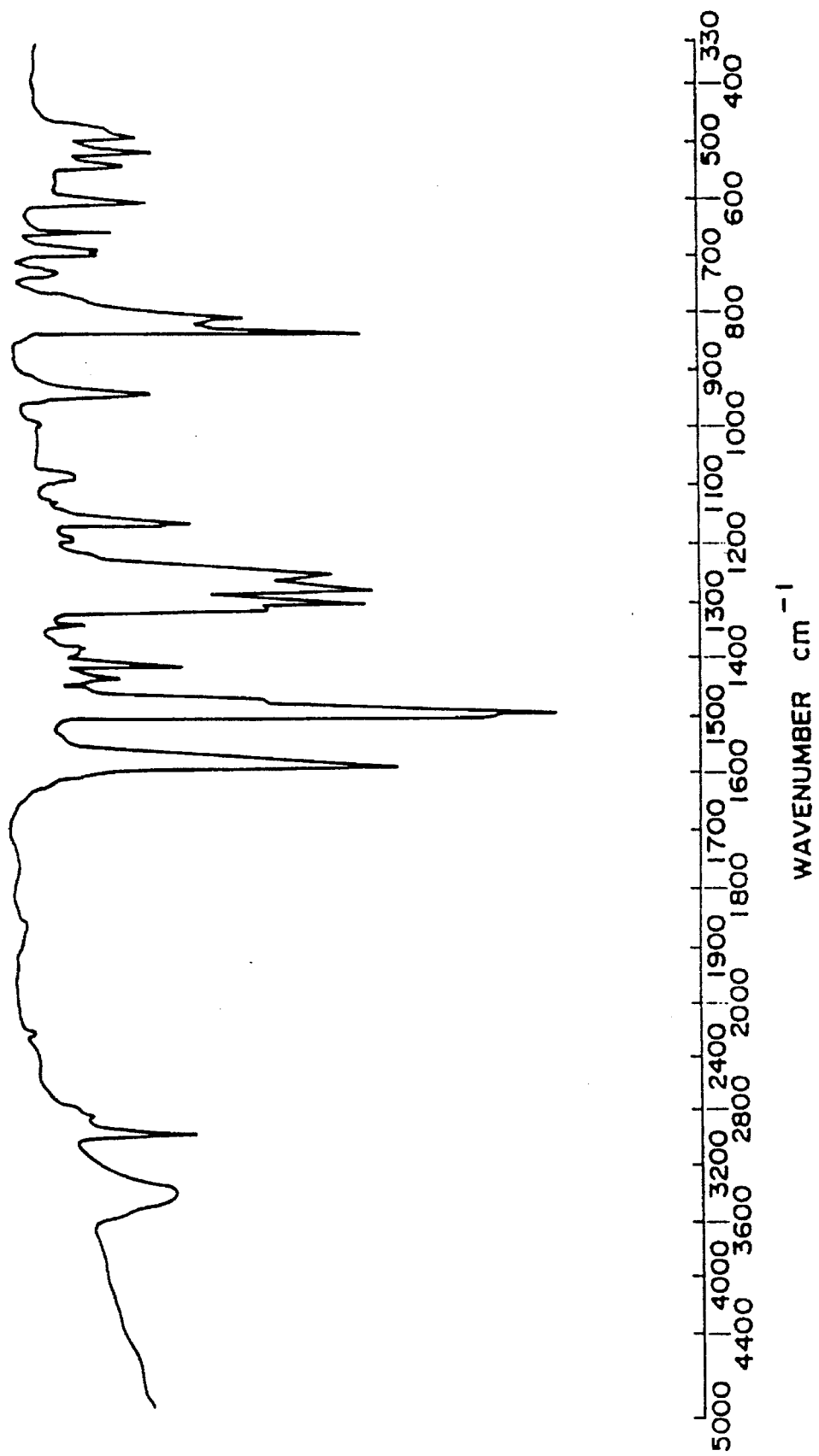
FIG. 10 is an IR absorption spectrum of 1,4-bis-[N-(1-pyrenyl)-N-(4-methylphenyl)-4-aminostyryl]benzene obtained in Example 2-2 by use of a KBr tablet.

FIG. 10 shows an IR absorption spectrum of the 1,4-bis-[N-(1-pyrenyl)-N-(4-methylphenyl)-4-aminostyryl]benzene taken by use of a KBr tablet.

The IR absorption spectrum of the above obtained compound indicates the appearance of the characteristic absorption peak based on the C-H out-of-plane deformation vibration of the trans-olefin in the compound at 960 cm⁻¹.

EXAMPLES 2-3 to 2-12

The procedure for preparation of N-(4-methylphenyl)-N-(4-styrylphenyl)-1-aminopyrene in Example 2-1 was repeated except that the diethyl benzylphosphonate used in Example 2-1 was replaced by the respective phosphorus compounds shown in TABLE 3, whereby pyrenylamine derivatives of the present invention were obtained as given in TABLE 3.

TABLE 3

| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C | % H | % N |
| 2-3 | [Ph₂CH—P(=O)(OEt)₂ structure] | [Pyrenyl-N(4-MeC₆H₄)(4-C₆H₄-CH=CPh₂) structure] | 177.0–180.5 (Ethanol-ethyl acetate) | 92.03 (91.94) | 5.49 (5.56) | 2.47 (2.49) |
| 2-4 | [PhCH=CH—CH₂—P(=O)(OEt)₂ structure] | [Pyrenyl-N(4-MeC₆H₄)(4-C₆H₄-CH=CH—CH=CH-Ph) structure] | 184.0–187.5 (Ethanol-ethyl acetate) | 91.56 (91.55) | 5.71 (5.71) | 2.74 (2.74) |

TABLE 3-continued

| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C | % H | % N |
| 2-5 | H₃C–⟨⟩–CH₂P(OEt)₂ (O=) | H₃C–⟨⟩–N(pyrenyl)(–⟨⟩–CH=CH–⟨⟩–CH₃) | 169.2–170.3 (Ethyl acetate-ethanol) | 91.09 (91.35) | 6.06 (5.85) | 2.89 (2.80) |
| 2-6 | H₃CO–⟨⟩–CH₂P(OEt)₂ (O=) | H₃C–⟨⟩–N(pyrenyl)(–⟨⟩–CH=CH–⟨⟩–OCH₃) | 180.0–181.0 (Toluene-ethanol) | 88.30 (88.51) | 5.75 (5.67) | 2.76 (2.72) |

TABLE 3-continued

| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C | % H | % N |
| 2-7 | [structure] | [structure] | 148.0–152.0 (Ethyl acetate-ethanol) | 91.31 (91.35) | 5.95 (5.85) | 2.87 (2.80) |
| 2-8 | [structure] | [structure] | 175.0–181.5 (Ethyl acetate-ethanol) | 91.71 (91.79) | 5.69 (5.78) | 2.45 (2.43) |

TABLE 3-continued

| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C. | % H | % N |
| 2-9 | O₂N–⌬–CH₂P(OEt)₂ (with O=) | H₃C–⌬–N(–⌬–CH=CH–⌬–NO₂)(pyrene) | 245.0–246.0 (Toluene-ethanol) | 84.00 (83.75) | 4.82 (4.94) | 5.16 (5.28) |
| 2-10 | H₂N–⌬–CH₂P(OEt)₂ (with O=) | H₃C–⌬–N(–⌬–CH=CH–⌬–NH₂)(pyrene) | 150.5–158.0 (Ethyl acetate-ethanol) | 89.00 (88.77) | 5.54 (5.64) | 5.46 (5.60) |
| 2-11 | ⌬–S–CH₂P(OEt)₂ (with O=) | H₃C–⌬–N(–⌬–CH=CH–S–⌬)(pyrene) | 180.0–184.5 (Toluene-ethanol) | 86.01 (85.84) | 5.08 (5.26) | 2.66 (2.71) |

TABLE 3-continued

| Ex. No. | Phosphorus Compound | Pyrenylamine Derivative having an unsaturated bond | Melting Point (°C.) (Solvent for Re-crystallization) | Elemental Analysis Found (Calcd.) | | |
|---|---|---|---|---|---|---|
| | | | | % C. | % H | % N |
| 2-12 | [(C₆H₅)₃—PCH₃]⁺ Br⁻ | H₃C—C₆H₄—N(—C₆H₄—CH=CH₂)(pyrenyl) | 170.0–174.0 (Toluene-ethanol) | 91.11 (90.92) | 5.55 (5.66) | 3.34 (3.42) |

EXAMPLES 2-13 to 2-18

The procedure for preparation of N-(4-methylphenyl)-N-(4-styrylphenyl)-1-aminopyrene in Example 2-1 was repeated except that the N-(4-formylphenyl)-N-(4-methylphenyl)-1-aminopyrene and the diethyl benzylphosphonate employed in Example 2-1 were respectively replaced by the aldehyde compounds and the phosphorus compounds shown in TABLE 4, whereby pyrenylamine derivatives of the present invention were obtained as given in TABLE 4.

TABLE 4
| Ex. No. | Aldehyde Compound | Phosphorus Compound | Pyrenylamine Derivative having an unsaturated bond | Melting Point (°C.) (Solvent for Recrystal- lization) | Elemental Analysis Found (Calcd.) | | |
|---|---|---|---|---|---|---|---|
| | | | | | % C | % H | % N |
| 2-13 | 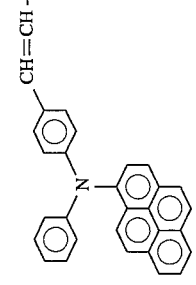 | 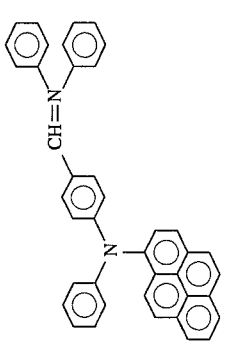 | 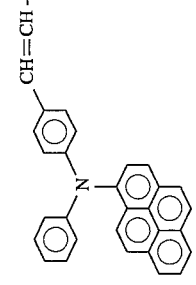 | 154.0–157.0 (Ethyl acetate- ethanol) | 91.32 (91.69) | 5.48 (5.34) | 2.95 (2.97) |
| 2-14 | 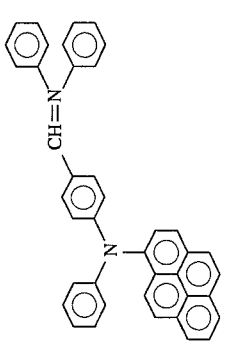 | 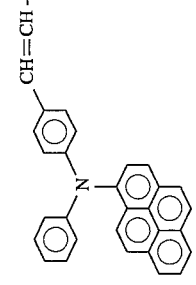 | 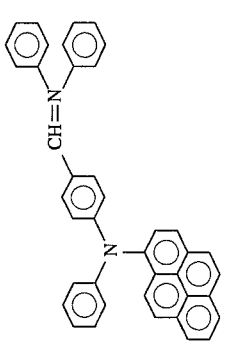 | 162.0–166.0 (Ethyl acetate- ethanol) | 91.98 (92.10) | 5.40 (5.34) | 2.72 (2.56) |
| 2-15 | 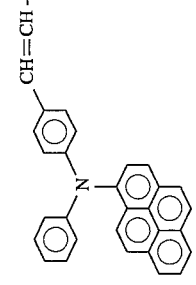 | CH=CH—CH$_2$P(OEt)$_2$ with =O | (structure) | 208.0–213.0 (Toluene- ethanol) | 91.71 (91.71) | 5.60 (5.47) | 2.72 (2.82) |
| 2-16 | 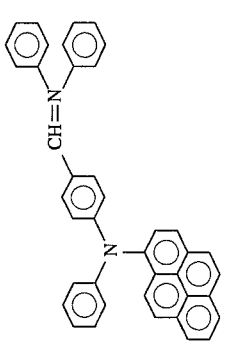 | (structure) | (structure) | Amorphous | 92.17 (91.94) | 5.23 (5.56) | 2.37 (2.50) |

TABLE 4-continued

| Ex. No. | Aldehyde Compound | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|---|
| | | | | | % C | % H | % N |
| 2-17 | (phenyl)–CH=CH–CH₂P(O)(OEt)₂ | (4-H₃C-C₆H₄)–N(pyrenyl)(4-CHO-C₆H₄) | (4-H₃C-C₆H₄)–N(pyrenyl)(C₆H₄–CH=CH–CH=CH–phenyl) | Amorphous | 91.83 (91.96) | 5.44 (5.66) | 2.22 (2.38) |
| 2-18 | [(C₆H₅)₃PCH₃]⁺Br⁻ | (phenyl)–N(pyrenyl)(4-CHO-C₆H₄) | (phenyl)–N(pyrenyl)(4-(CH=CH₂)-C₆H₄) | 157.0–158.0 (Toluene-n-hexane) | 91.29 (91.10) | 5.24 (5.36) | 3.47 (3.54) |

EXAMPLE 2-19

The procedure for preparation of 1,4-bis-[N-(1-pyrenyl)-N-(4-methylphenyl)-4-aminostyryl]benzene in Example 2-2 was repeated except that the N-(4-formylphenyl)-N-(4-methylphenyl)-1-aminopyrene and tetraethyl p-xylylenediphosphonate used in Example 2-2 were respectively replaced by the aldehyde compound and the phosphorus compound shown in the following reaction scheme, whereby a pyrenylamine derivative according to the present invention was obtained:

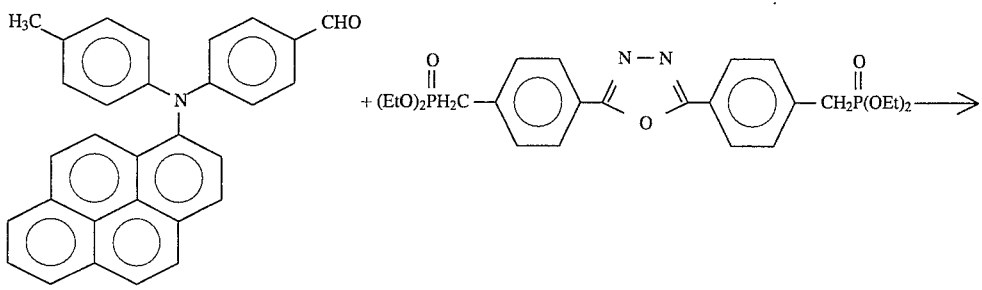

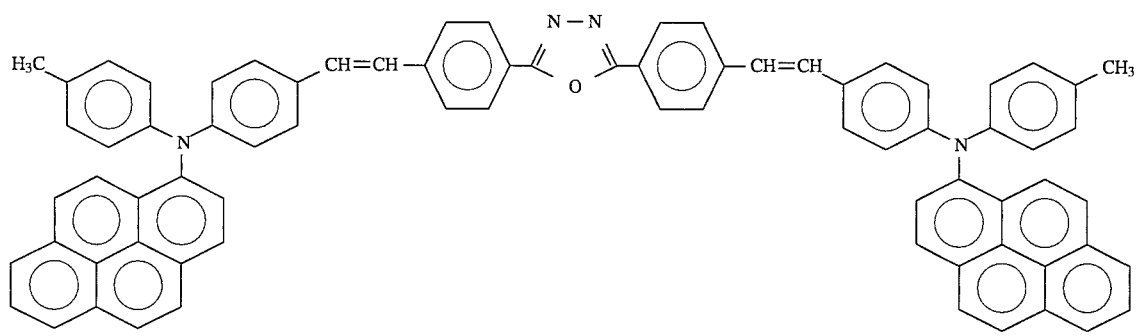

The melting point of the above compound which was recrystallized from toluene was 250.0° C. or more.

The results of the elemental analysis of the above compound were as follows:

|       | % C   | % H  | % N  |
|-------|-------|------|------|
| Found | 88.24 | 4.96 | 5.29 |
| Calcd.| 88.00 | 5.05 | 5.40 |

EXAMPLE 2-20

[Synthesis of N-(4-methoxyphenyl)-N-(4-styrylphenyl)-1-aminopyrene (Compound No. 41 in TABLE 1)]

0.82 g (2.7 mmol) of 4-(4-methoxyphenyl)aminostilbene, 1.34 g (4.1 mmol) of 1-iodopyrene, 0.56 g (4.1 mmol) of potassium carbonate and 0.10 g of copper powder were added to 20 ml of nitrobenzene. The above mixture was refluxed for 15 hours while azeotropic dehydration was being carried out under a stream of nitrogen.

After the mixture was cooled to room temperature, the resulting insoluble material in the mixture was removed therefrom by filtration. The solvent was distilled away from the resulting mixture under reduced pressure with the application of heat thereto. The residue thus obtained was dissolved in toluene, washed with water, and dried over magnesium sulfate. The solvent was distilled away from the mixture under reduced pressure with the application of heat thereto, so that an oily dark brown material was obtained.

The oily material thus obtained was subjected to column chromatography using silica gel as a carrier and a mixed solvent of toluene and n-hexane with a volume ratio of 4:1 as an eluting solution to obtain a product. The product was recrystallized from a mixed solvent of ethyl acetate and ethanol, so that 0.98 g of N-(4-methoxyphenyl)-N-(4-styrylphenyl)-1-aminopyrene (Compound No. 41) was obtained in a yield of 72.6%.

The melting point of the above compound was 145.2° C. (TG-DTA endothermic peak temperature).

The result of the elemental analysis of the compound were as follows:

|       | % C   | % H  | % N  |
|-------|-------|------|------|
| Found | 88.39 | 5.38 | 2.81 |
| Calcd.| 88.58 | 5.44 | 2.79 |

The above calculation was based on the formula for N-(4-methoxyphenyl)-N-(4-styrylphenyl)-1-aminopyrene of $C_{37}H_{27}NO$.

EXAMPLE 2-21

[Synthesis of N-(4-methoxyphenyl)-N-(4-β-phenylstyrylphenyl)-1-aminopyrene (Compound No. 42 in TABLE 1)]

The procedure for preparation of N-(4-methoxyphenyl)-N-(4-styrylphenyl)-1-aminopyrene in Example 2-20 was repeated except that the 4-(4-methoxyphenyl)aminostilbene used in Example 2-20 was replaced by 4'-(4-methoxyphenyl)-amino-α-phenylstilbene, so that N-(4-methoxyphenyl)-N-(4-β-phenylstyrylphenyl)-1-aminopyrene (Compound No. 42) was obtained.

The melting point of the above compound was 183.2° C. (TG-DTA endothermic peak temperature).

The results of the elemental analysis of the compound were as follows:

|       | % C   | % H  | % N  |
|-------|-------|------|------|
| Found | 89.48 | 5.41 | 2.39 |
| Calcd.| 89.39 | 5.42 | 2.42 |

The above calculation was based on the formula for N-(4-methoxyphenyl)-N-(4-β-phenylstyrylphenyl)-1-aminopyrene of $C_{43}H_{31}NO$.

EXAMPLE 3-1

76 parts by weight of Diane Blue (C.I. Pigment Blue 25: C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and pulverized in a ball mill. The thus obtained dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

2 parts by weight of the N-(4-methylphenyl)-N-(4-styrylphenyl)-1-aminopyrene synthesized in Example 2-1 (Compound No. 1) serving as a charge transporting material, 2 parts by weight of polycarbonate resin (Trademark "Panlite K1300" made by Teijin Limited) and 16 parts by weight of tetrahydrofuran were mixed and dissolved to prepare a coating liquid for a charge transport layer. The thus obtained coating liquid was coated on the above formed charge generation layer by a doctor blade, ad dried at 80° C. for 2 minutes and then at 120° C. for 5 minutes, so that a charge transport layer with a thickness of about 20 μm was formed on the charge generation layer. Thus, electrophotographic photoconductor No. 1 according to the present invention was fabricated.

EXAMPLES 3-2 to 3-81

The procedure for preparation of electrophotographic photoconductor No. 1 in Example 3-1 was repeated except that Diane Blue serving as a charge generating material for use in the charge generation layer and the Compound No. 1 serving as a charge transporting material for use in the charge transport layer in Example 3-1 were respectively replaced by each of the charge generating materials and charge transporting materials listed in the following TABLE 5, whereby electrophotographic photoconductors No. 2 to No. 81 according to the present invention were fabricated.

TABLE 5

| Example No. | Charge Generating Material | Charge Transporting Material (Pyrenylamine Derivative) |
|---|---|---|
| 3-1 | (bis-azo compound with two hydroxynaphthalene-CONHPh groups linked via N=N to a biphenyl bearing two OCH₃ groups) | Compound No. 1 |
| 3-2 | (bis-azo compound with two hydroxynaphthalene-CONHPh groups linked via N=N to a biphenyl bearing two Cl groups) | Compound No. 1 |
| 3-3 | (bis-azo compound with two hydroxynaphthalene-CONH(2-CH₃-4-CH₃-phenyl) groups linked via N=N to a bis(styryl)benzene-type system with −CH=CH− linkages) (hereinafter referred to as P-1.) | Compound No. 1 |

TABLE 5-continued

| Example No. | Charge Generating Material | Charge Transporting Material (Pyrenylamine Derivative) |
|---|---|---|
| 3-4 | (structure) | Compound No. 1 |
| 3-5 | (structure) (hereinafter referred to as P-2.) | Compound No. 1 |
| 3-6 | (structure) (hereinafter referred to as P-3.) | Compound No. 1 |

TABLE 5-continued

| Example No. | Charge Generating Material | Charge Transporting Material (Pyrenylamine Derivative) |
|---|---|---|
| 3-7 | β-type Copper Phthalocyanine | Compound No. 1 |
| 3-8 | [azo dye structure with OCH₃/H₃CO substituents, naphthol groups with CONH-phenyl and HNOC-phenyl amide groups] | Compound No. 2 |
| 3-9 | [azo dye structure with Cl substituents, naphthol groups with CONH-phenyl and HNOC-phenyl amide groups] | Compound No. 2 |
| 3-10 | P-1 | Compound No. 2 |
| 3-11 | P-2 | Compound No. 2 |
| 3-12 | P-3 | Compound No. 2 |
| 3-13 | P-1 | Compound No. 3 |
| 3-14 | P-2 | Compound No. 3 |
| 3-15 | P-3 | Compound No. 3 |
| 3-16 | P-1 | Compound No. 41 |
| 3-17 | P-2 | Compound No. 41 |
| 3-18 | P-3 | Compound No. 41 |
| 3-19 | P-1 | Compound No. 42 |
| 3-20 | P-2 | Compound No. 42 |
| 3-21 | P-3 | Compound No. 42 |
| 3-22 | P-1 | Compound No. 4 |
| 3-23 | P-2 | Compound No. 4 |
| 3-24 | P-3 | Compound No. 4 |
| 3-25 | P-1 | Compound No. 5 |
| 3-26 | P-2 | Compound No. 5 |
| 3-27 | P-3 | Compound No. 5 |
| 3-28 | P-1 | Compound No. 6 |

TABLE 5-continued

| Example No. | Charge Generating Material | Charge Transporting Material (Pyrenylamine Derivative) |
|---|---|---|
| 3-29 | P-2 | Compound No. 6 |
| 3-30 | P-3 | Compound No. 6 |
| 3-31 | P-1 | Compound No. 68 |
| 3-32 | P-2 | Compound No. 68 |
| 3-33 | P-3 | Compound No. 68 |
| 3-34 | P-1 | Compound No. 18 |
| 3-35 | P-2 | Compound No. 18 |
| 3-36 | P-3 | Compound No. 18 |
| 3-37 | P-1 | Compound No. 74 |
| 3-38 | P-2 | Compound No. 74 |
| 3-39 | P-3 | Compound No. 74 |
| 3-40 | P-1 | Compound No. 51 |
| 3-41 | P-2 | Compound No. 51 |
| 3-42 | P-3 | Compound No. 51 |
| 3-43 | P-1 | Compound No. 53 |
| 3-44 | P-2 | Compound No. 53 |
| 3-45 | P-3 | Compound No. 53 |
| 3-46 | P-1 | Compound No. 75 |
| 3-47 | P-2 | Compound No. 75 |
| 3-48 | P-3 | Compound No. 75 |
| 3-49 | P-1 | Compound No. 15 |
| 3-50 | P-2 | Compound No. 15 |
| 3-51 | P-3 | Compound No. 15 |
| 3-52 | P-1 | Compound No. 76 |
| 3-53 | P-2 | Compound No. 76 |
| 3-54 | P-3 | Compound No. 76 |
| 3-55 | P-1 | Compound No. 16 |
| 3-56 | P-2 | Compound No. 16 |
| 3-57 | P-3 | Compound No. 16 |
| 3-58 | P-1 | Compound No. 77 |
| 3-59 | P-2 | Compound No. 77 |
| 3-60 | P-3 | Compound No. 77 |
| 3-61 | P-1 | Compound No. 78 |
| 3-62 | P-2 | Compound No. 78 |
| 3-63 | P-3 | Compound No. 78 |
| 3-64 | P-1 | Compound No. 11 |
| 3-65 | P-2 | Compound No. 11 |
| 3-66 | P-3 | Compound No. 11 |
| 3-67 | P-1 | Compound No. 12 |
| 3-68 | P-2 | Compound No. 12 |
| 3-69 | P-3 | Compound No. 12 |
| 3-70 | P-1 | Compound No. 20 |
| 3-71 | P-2 | Compound No. 20 |
| 3-72 | P-3 | Compound No. 20 |
| 3-73 | P-1 | Compound No. 31 |
| 3-74 | P-2 | Compound No. 31 |
| 3-75 | P-3 | Compound No. 31 |
| 3-76 | P-1 | Compound No. 32 |

TABLE 5-continued

| Example No. | Charge Generating Material | Charge Transporting Material (Pyrenylamine Derivative) |
|---|---|---|
| 3-77 | P-2 | Compound No. 32 |
| 3-78 | P-3 | Compound No. 32 |
| 3-79 | P-1 | Compound No. 33 |
| 3-80 | P-2 | Compound No. 33 |
| 3-81 | P-3 | Compound No. 33 |

EXAMPLE 3-82

Selenium was vacuum-deposited on an aluminum plate with a thickness of about 300 μm, so that a charge generation layer with a thickness of about 1 μm was formed on the aluminum plate.

2 parts by weight of the pyrenylamine derivative (Compound No. 1), 3 parts by weight of polyester resin (Trademark "Polyester Adhesive 49000" made by Du Pont de Nemours, E.I. & Co.) and 45 parts by weight of tetrahydrofuran were mixed and dissolved to prepare a coating liquid for a charge transport layer. The thus prepared coating liquid was coated on the above formed charge generation layer by a doctor blade, and dried at room temperature and then under reduced pressure, so that a charge transport layer with a thickness of about 10 μm was formed on the charge generation layer. Thus, electrophotographic photoconductor No. 82 according to the present invention was fabricated.

EXAMPLE 3-83

The procedure for preparation of the electrophotographic photoconductor No. 49 in Example 3-82 was repeated except that a charge generation layer with a thickness of about 0.6 μm was formed on the same aluminum plate as employed in Example 3-82 by deposition of the following perylene pigment instead of selenium, and the charge transporting material employed in Example 3-82 was replaced by a pyrenylamine derivative (Compound No. 1) serving as a charge transporting material, so that electrophotographic photoconductor No. 83 according to the present invention was fabricated:

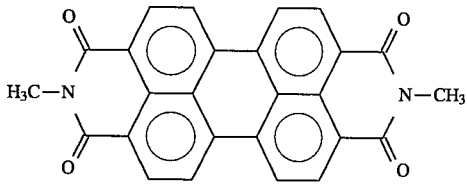

EXAMPLE 3-84

1 part by weight of the same Diane Blue as employed in Example 3-1 and 158 parts by weight of tetrahydrofuran were mixed and pulverized in a ball mill to prepare a mixture. To the thus prepared mixture, 12 parts by weight of a pyrenylamine derivative (Compound No. 1) and 18 parts by weight of polyester resin (Trademark "Polyester Adhesive 49000" made by Du Pont de Nemours, E.I. & Co.) were added to prepare a coating liquid for a photoconductive layer. The thus prepared coating liquid was coated on an aluminum-deposited polyester film serving as an electroconductive substrate by a doctor blade, and dried at 100° C. for 30 minutes, so that a photoconductive layer with a thickness of about 16 μm was formed on the electroconductive substrate. Thus, electrophotographic photoconductor No. 84 according to the present invention was fabricated.

EXAMPLE 3-85

2 parts by weight of the Compound No. 1 serving as a charge transporting material, 2 parts by weight of polycarbonate resin (Trademark "Panlite K-1300" made by Teijin Limited) and 16 parts by weight of tetrahydrofuran were mixed to prepare a coating liquid for a charge transport layer. The thus prepared coating liquid was coated on an aluminum-deposited polyester film serving as an electroconductive substrate by a doctor blade, and dried at 80° C. for 2 minutes and then at 120° C. for 5 minutes, so that a charge transport layer with a thickness of about 20 μm was formed on the electroconductive substrate.

13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve were mixed and pulverized in a ball mill to prepare a mixture. To the thus prepared mixture, 1700 parts by weight of ethyl cellosolve were further added and stirred to prepare a coating liquid for a charge generation layer. The thus prepared coating liquid was coated on the above formed charge transport layer by spray coating and dried at 100° C. for 10 minutes, so that a charge generation layer with a thickness of about 0.2 μm was formed on the charge transport layer.

A methanol—n-butanol solution of a polyamide resin (Trademark "CM-8000" made by Toray Industries, Inc.) was coated on the above formed charge generation layer by spray coating and dried at 120° C. for 30 minutes, so that a protective layer with a thickness of about 0.5 μm was formed on the charge generation layer. Thus, an electrophotographic photoconductor No. 85 according to the present invention was fabricated.

Each of the thus fabricated electrophotographic photoconductors No. 1 to No. 85 according to the present invention was charged under application of −6 kV or +6 kV of corona charge for 20 seconds, using a commercially available electrostatic copying sheet testing apparatus ("Paper Analyzer Model SP428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux·sec) required to reduce the initial surface potential Vpo (V) to ½ thereof was measured. The results are shown in TABLE 6.

Furthermore, each of the electrophotographic photoconductors No. 1 to No. 85 according to the present invention was charged by use of a commercially available electrophotographic copying machine. Then, a latent electrostatic image was formed on the photoconductor using an original by illuminating the charged photoconductor. The thus formed latent electrostatic image was developed by a dry-type developer to a visible image. The thus obtained toner image was electrostatically transferred and fixed onto a sheet of normal paper, so that a clear transferred image was obtained. A clear image was also obtained when a wet-type developer was employed for development of the latent electrostatic image.

TABLE 6

| Photoconductor No. | Vpo(V) | $E_{1/2}$(lux.sec) |
| --- | --- | --- |
| 1 | −1220 | 1.40 |
| 2 | −1160 | 1.23 |
| 3 | −1200 | 0.95 |
| 4 | −1245 | 1.98 |
| 5 | −1215 | 0.86 |
| 6 | −794 | 0.43 |
| 7 | −1240 | 1.81 |
| 8 | −1235 | 1.45 |
| 9 | −1080 | 1.18 |
| 10 | −1095 | 1.02 |

TABLE 6-continued

| Photoconductor No. | Vpo(V) | E₁/₂(lux.sec) |
|---|---|---|
| 11 | −1186 | 0.91 |
| 12 | −983 | 0.52 |
| 13 | −1178 | 0.70 |
| 14 | −865 | 0.68 |
| 15 | −825 | 0.40 |
| 16 | −1129 | 0.98 |
| 17 | −1080 | 0.80 |
| 18 | −745 | 0.42 |
| 19 | −1201 | 1.01 |
| 20 | −1107 | 0.86 |
| 21 | −832 | 0.48 |
| 22 | −1253 | 1.14 |
| 23 | −1149 | 1.02 |
| 24 | −812 | 0.50 |
| 25 | −1218 | 0.91 |
| 26 | −1060 | 0.80 |
| 27 | −662 | 0.37 |
| 28 | −1285 | 0.92 |
| 29 | −1136 | 0.80 |
| 30 | −993 | 0.49 |
| 31 | −1293 | 0.96 |
| 32 | −1136 | 0.85 |
| 33 | −1012 | 0.50 |
| 34 | −1314 | 1.07 |
| 35 | −1220 | 0.95 |
| 36 | −807 | 0.45 |
| 37 | −1286 | 1.19 |
| 38 | −1177 | 0.94 |
| 39 | −721 | 0.40 |
| 40 | −1510 | 1.21 |
| 41 | −1393 | 1.06 |
| 42 | −703 | 0.39 |
| 43 | −1332 | 1.09 |
| 44 | −1190 | 0.92 |
| 45 | −752 | 0.41 |
| 46 | −1489 | 1.21 |
| 47 | −1316 | 1.08 |
| 48 | −774 | 0.41 |
| 49 | −1105 | 1.04 |
| 50 | −1166 | 0.97 |
| 51 | −964 | 0.49 |
| 52 | −1167 | 1.40 |
| 53 | −1194 | 1.21 |
| 54 | −769 | 0.44 |
| 55 | −1365 | 2.48 |
| 56 | −1399 | 2.01 |
| 57 | −899 | 0.53 |
| 58 | −1203 | 1.96 |
| 59 | −1281 | 1.62 |
| 60 | −950 | 0.54 |
| 61 | −1097 | 1.46 |
| 62 | −1153 | 1.32 |
| 63 | −891 | 0.51 |
| 64 | −1163 | 1.21 |
| 65 | −1201 | 1.01 |
| 66 | −824 | 0.50 |
| 67 | −1038 | 0.96 |
| 68 | −1090 | 0.80 |
| 69 | −671 | 0.39 |
| 70 | −1080 | 1.96 |
| 71 | −1215 | 1.68 |
| 72 | −861 | 0.57 |
| 73 | −1201 | 1.21 |
| 74 | −1273 | 0.98 |
| 75 | −768 | 0.46 |
| 76 | −1238 | 1.23 |
| 77 | −1301 | 1.06 |
| 78 | −790 | 0.46 |
| 79 | −1211 | 1.22 |
| 80 | −1281 | 0.98 |
| 81 | −780 | 0.45 |
| 82 | −983 | 1.96 |
| 83 | −1285 | 2.87 |
| 84 | +1293 | 1.58 |
| 85 | +1284 | 0.89 |

The electrophotographic photoconductors having pyrenylamine derivatives of formula (I) according to the present invention exhibit a significantly improved resistance to heat and mechanical shocks as well as excellent photoconductive properties. Furthermore, the photoconductors according to the present invention can be manufactured at a low cost.

In addition, the pyrenylamine derivatives of formula (Ia) for use in the electrophotographic photoconductors according to the present invention are useful as organic photoconductive materials and fluorescent whitening agents for use in electrophotographic photoconductors. In particular, when the pyrenylamine derivatives are employed as the organic photoconductive materials for use in electrophotographic photoconductors, the fundamental characteristics necessary for the photoconductors can be satisfied and photoconductors having flexibility can also be provided.

What is claimed is:

1. A method of preparing a pyrenylamine derivative of formula (Ia) comprising the step of allowing a secondary amine compound of formula (IV) to react with a pyrene compound of formula (V) in accordance with the following reaction scheme:

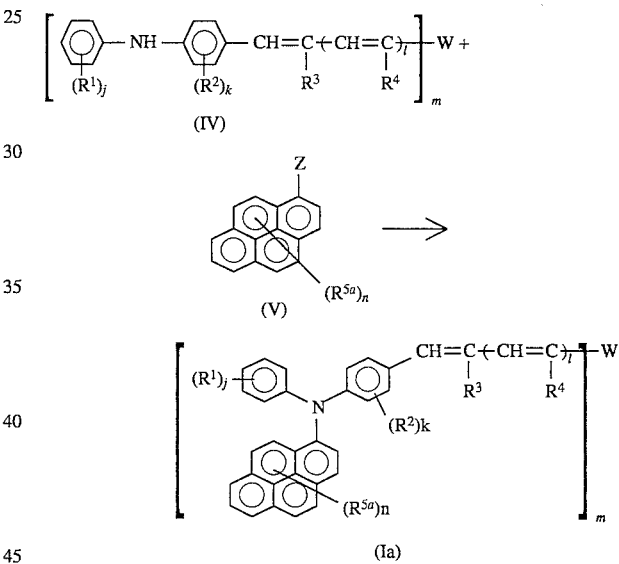

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or a phenyl group; $R^3$ and $R^4$ each represent hydrogen, cyano group, formyl group, an alkoxycarbonyl group, an alkyl group having 1 to 10 carbon atoms, an alkenyl group having 1 to 10 carbon atoms, or a phenyl group; $R^{5a}$ represents hydrogen, or an alkyl group having 1 to 10 carbon atoms; W represents hydrogen, an alkyl group having 1 to 10 carbon atoms, a phenylthio group, a bivalent chain unsaturated hydrocarbon group, a monovalent or bivalent carbocyclic aromatic group, or a monovalent or bivalent heterocyclic hydrocarbon group; and j is an integer of 1 to 5, k is an integer of 1 to 4, l is an integer of 0 to 2, m is an integer of 1 or 2, n is an integer of 1 to 3, provided that when j, k or n is 2 or more, $R^1$, $R^2$, or $R^{5a}$ may be the same or different; and Z represents a halogen atom.

* * * * *

UNITED STATES PATENT AND TRADEMARK OFFICE
CERTIFICATE OF CORRECTION

PATENT NO. : 5,587,516
DATED : December 24, 1996
INVENTOR(S) : Chiaki TANAKA, et al.

It is certified that error appears in the above-identified patent and that said Letters Patent is hereby corrected as shown below:

Column 8, line 23, "$R^9$ and $R^{10}$ and R" should read
--$R^9$ and $R^{10}$--.

Column 35, line 45, "pyrenylamine derivative" should
read --pyrenylamine derivatives--.

Column 66, line 38, "The result" should read
--The results--.

Column 68, line 7, "ad dried" should read --and dried--.

Signed and Sealed this

Twenty-fourth Day of March, 1998

Attest:

BRUCE LEHMAN

Attesting Officer      Commissioner of Patents and Trademarks